United States Patent
Kasahara et al.

(10) Patent No.: US 9,433,385 B2
(45) Date of Patent: Sep. 6, 2016

(54) BLOOD SUGAR LEVEL MEASURING DEVICE AND BLOOD SUGAR LEVEL MEASURING METHOD

(71) Applicant: SEIKO EPSON CORPORATION, Tokyo (JP)

(72) Inventors: Hirokazu Kasahara, Okaya (JP); Kimitake Mizobe, Pittsburgh, PA (US); Hideto Ishiguro, Shiojiri (JP)

(73) Assignee: SEIKO EPSON CORPORATION, Tokyo (JP)

( * ) Notice: Subject to any disclaimer, the term of this patent is extended or adjusted under 35 U.S.C. 154(b) by 78 days.

(21) Appl. No.: 14/600,467

(22) Filed: Jan. 20, 2015

(65) Prior Publication Data

US 2015/0216482 A1 Aug. 6, 2015

(30) Foreign Application Priority Data

Jan. 31, 2014 (JP) ................................. 2014-017025

(51) Int. Cl.
| | |
|---|---|
| A61B 5/11 | (2006.01) |
| A61B 5/00 | (2006.01) |
| A61B 5/145 | (2006.01) |
| A61B 5/1455 | (2006.01) |
| A61B 5/1495 | (2006.01) |

(52) U.S. Cl.
CPC ............ *A61B 5/7275* (2013.01); *A61B 5/1118* (2013.01); *A61B 5/1455* (2013.01); *A61B 5/1495* (2013.01); *A61B 5/14532* (2013.01); *A61B 5/4866* (2013.01); *A61B 5/681* (2013.01); *A61B 2560/0209* (2013.01)

(58) Field of Classification Search
None
See application file for complete search history.

(56) References Cited

U.S. PATENT DOCUMENTS

| | | | |
|---|---|---|---|
| 6,005,658 A | 12/1999 | Kaluza et al. | |
| 7,313,426 B2 | 12/2007 | Takeda et al. | |
| 2006/0264895 A1* | 11/2006 | Flanders | ............... A61M 5/14 604/504 |
| 2008/0045819 A1* | 2/2008 | Emoto | ............... A61B 5/0002 600/316 |
| 2008/0114299 A1* | 5/2008 | Damgaard-Sorensen | ............ G06F 19/3406 604/131 |
| 2011/0201909 A1* | 8/2011 | Emery | ............... A61B 5/14532 600/322 |
| 2013/0053700 A1* | 2/2013 | Ignotz | ............... A61B 3/1173 600/476 |
| 2014/0120564 A1* | 5/2014 | Workman | ......... A61B 5/14532 435/14 |

FOREIGN PATENT DOCUMENTS

| | | |
|---|---|---|
| EP | 2 479 575 A1 | 7/2012 |
| JP | H10-314150 A | 12/1998 |
| JP | 2005-278758 A | 10/2005 |
| JP | 2011-064596 A | 3/2011 |
| JP | 2014-124453 A | 7/2014 |
| JP | 2014-124454 A | 7/2014 |
| JP | 2014-124455 A | 7/2014 |

* cited by examiner

*Primary Examiner* — Brian T Gedeon
*Assistant Examiner* — Ankit D Tejani
(74) *Attorney, Agent, or Firm* — Oliff PLC

(57) ABSTRACT

In a blood sugar level measuring device, a blood-sugar-level predicting unit predicts a blood sugar level of a user. A light emitting unit irradiates measurement light to the inside of a living organism of the user. A light-emission control unit, a measurement-point-candidate setting unit, a light-amount-control-method determining unit, and a measurement-point selecting unit control a light amount of measurement light per one measurement on the basis of the predicted blood sugar level. A light-reception control unit, a light-absorption-spectrum generating unit, and a blood-sugar-value calculating unit receive reflected light from the user and measure a blood sugar level.

11 Claims, 14 Drawing Sheets

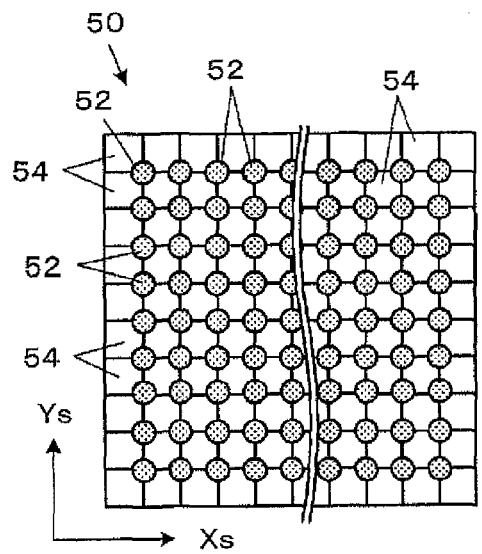
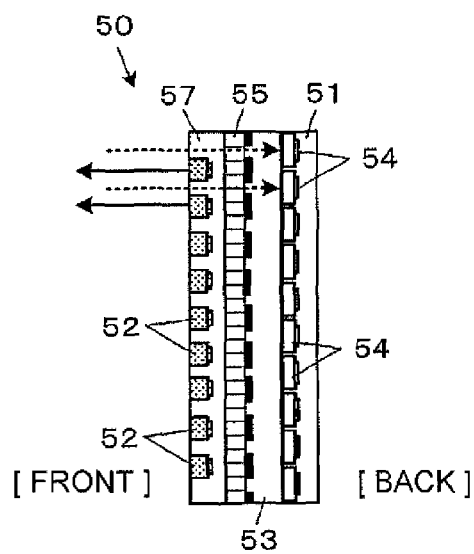
FIG. 2A     FIG. 2B
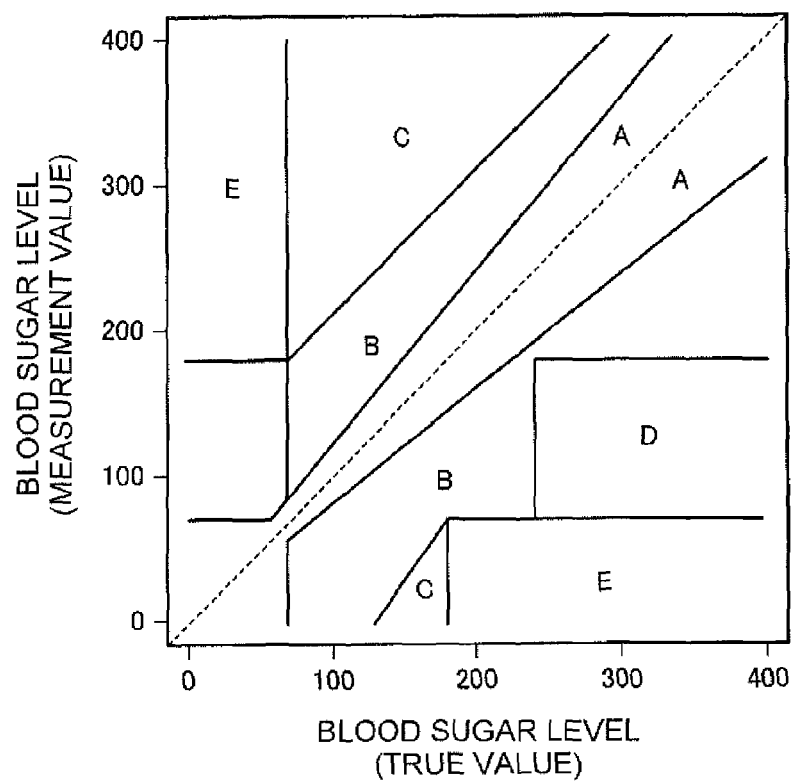
FIG. 3

186

| PREDICTED BLOOD SUGAR LEVEL | LIGHT AMOUNT CONTROL METHOD ||
|---|---|---|
| | CONTROL METHOD TYPE | NUMBER OF LIGHT EMITTING ELEMENTS |
| SMALLER THAN PREDETERMINED THRESHOLD (PREDICTED BLOOD SUGAR LEVEL : LOW) | FIRST LIGHT AMOUNT CONTROL METHOD | $D_{21}$ |
| EQUAL TO OR LARGER THAN PREDETERMINED THRESHOLD (PREDICTED BLOOD SUGAR LEVEL : HIGH) | SECOND LIGHT AMOUNT CONTROL METHOD | $D_{23}$ |

| ADJUSTMENT CONDITION | ADJUSTMENT AMOUNT |
|---|---|
| EXERCISE INTENSITY : AT $D_{311}$ TO $D_{313}$ DURATION : $T_{31}$ MINUTES OR LONGER (EXERCISE STATE : NORMAL) | $S_{31}$ |
| EXERCISE INTENSITY : AT $D_{331}$ OR MORE DURATION : $T_{33}$ MINUTES OR LONGER (EXERCISE STATE : INTENSE) | $S_{33}$ |
| ⋮ | ⋮ |

| MEASUREMENT DATE AND TIME | EXERCISE INTENSITY | MEAL INFORMATION | | INSULIN ADMINISTRATION INFORMATION |
| --- | --- | --- | --- | --- |
| | | MEAL START | MEAL MENU | |
| ⋮ | ⋮ | ⋮ | ⋮ | ⋮ |
| 2014.1.15 7:30 | xxxxx | − | − | ○ |
| 2014.1.15 7:31 | xxxxx | − | − | − |
| 2014.1.15 7:32 | xxxxx | − | − | − |
| ⋮ | ⋮ | ⋮ | ⋮ | ⋮ |
| 2014.1.15 11:59 | xxxxx | − | − | − |
| 2014.1.15 12:00 | xxxxx | ○ | MEAL MENU A | − |
| 2014.1.15 12:01 | xxxxx | − | − | − |
| ⋮ | ⋮ | ⋮ | ⋮ | ⋮ |

FIG.14

BLOOD SUGAR LEVEL MEASURING DEVICE AND BLOOD SUGAR LEVEL MEASURING METHOD

This application claims the benefit of Japanese Patent Application No. 2014-017025, filed on Jan. 31, 2014. The content of the aforementioned application is incorporated herein by reference in its entirety.

BACKGROUND

1. Technical Field

The present invention relates to a blood sugar level measuring device and the like that measure a blood sugar level of a user.

2. Related Art

There is known a blood sugar level measuring device that noninvasively measures glucose concentration, that is, a blood sugar level in blood using light. Since the blood sugar level greatly fluctuates even in a day because of meals, exercise, and the like, the blood sugar level needs to be frequently measured. Therefore, for diabetics and the like to measure and manage blood sugar levels by themselves, there is a demand for a portable blood sugar level measuring device for a continuous use. However, since the blood sugar level measuring device is portable, the blood sugar level measuring device relies on battery operation. A large capacity battery is desirable from the viewpoint of, for example, frequencies of charging and battery replacement. However, a small capacity battery small in size and weight is desirable from the viewpoint of portability. From all the viewpoints, an important technique is a technique for reducing power consumption.

As the technique for reducing power consumption, for example, a technique for intermittently performing measurement is disclosed in JP-A-10-314150 (Patent Literature 1).

Incidentally, continuous measurement of a blood sugar level is performed for the purpose of quick detection of a hypoglycemia state in which a blood sugar level is low. Since the hypoglycemia state is a fatal dangerous state, quick detection of the hypoglycemia state is requested. When the technique for intermittently performing measurement disclosed in Patent Literature 1 is adopted, if a set measurement interval is too long, there is a risk that detection of the hypoglycemia state is delayed. The measurement interval is desirably short for the quick detection of the hypoglycemia state. However, a reduction effect for power consumption is not expected too much.

SUMMARY

An advantage of some aspects of the invention is to attain a reduction in power consumption.

A first aspect of the invention is directed to a blood sugar level measuring device including: a predicting unit configured to predict a blood sugar level of a user; a light emitting unit for irradiating measurement light to the inside of a living organism of the user; a light-amount control unit configured to control a light amount of the measurement light per one measurement on the basis of the predicted blood sugar level; and a measuring unit configured to receive reflected light from the user and measure a blood sugar level.

As another aspect of the invention, the first aspect of the invention may be configured as a blood sugar level measuring method including: predicting a blood sugar level of a user; emitting measurement light to the inside of a living organism of the user; controlling a light amount of the measurement light per one measurement on the basis of the predicted blood sugar level; and receiving reflected light from the user and measuring a blood sugar level.

If the light amount of the measurement light per one measurement is reduced, power consumption can be suppressed. According to the first and another aspects, it is possible to predict a blood sugar level of the user and control the light amount of the measurement light per one measurement on the basis of the predicted blood sugar level. Therefore, it is possible to attain a reduction in power consumption.

A second aspect of the invention is directed to the blood sugar level measuring device according to the first aspect of the invention, wherein the predicting unit predicts a blood sugar level of the user on the basis of a blood sugar level measured in the past by the measuring unit.

According to the second aspect of the invention, it is possible to predict a blood sugar level of the user on the basis of a blood sugar level measured in the past.

A third aspect of the invention is directed to the blood sugar level measuring device according to the second aspect of the invention, wherein the predicting unit predicts a blood sugar level of the user on the basis of a transition of the blood sugar level measured in the past.

A fourth aspect of the invention is directed to the blood sugar level measuring device according to the second aspect of the invention, wherein the predicting unit predicts, as a blood sugar level of the user, a blood sugar level measured immediately before the prediction.

According to the third aspect of the invention, it is possible to predict a blood sugar level of the user on the basis of a transition of the blood sugar level measured in the past. According to the fourth aspect of the invention, it is possible to predict, as a blood sugar level of the user, a blood sugar level measured immediately before the prediction.

A fifth aspect of the invention is directed to the blood sugar level measuring device according to any of the first to fourth aspects of the invention, wherein the predicting unit adjusts the predicted blood sugar level on the basis of at least any one of presence or absence of a meal of the user and presence or absence of insulin administration.

A blood sugar level during a meal shows a rising tendency and a blood sugar level during insulin administration shows a falling tendency. According to the fifth aspect of the invention, it is possible to adjust the predicted blood sugar level on the basis of at least any one of presence or absence of a meal of the user and presence or absence of insulin administration. Therefore, it is possible to improve prediction accuracy of a blood sugar level.

A sixth aspect of the invention is directed to the blood sugar level measuring device according to the fifth aspect of the invention, wherein the predicting unit adjusts the predicted blood sugar level on the basis of dietary content of the user.

As explained above, a blood sugar level during a meal shows a rising tendency. However, a rising amount of the blood sugar level fluctuates according to dietary content. According to the sixth aspect of the invention, it is possible to adjust the predicted blood sugar level on the basis of dietary content of the user. Therefore, it is possible to further improve the prediction accuracy of a blood sugar level.

A seventh aspect of the invention is directed to the blood sugar level measuring device according to any of the first to sixth aspects of the invention, wherein the blood sugar level measuring device further includes a body-motion detecting unit for detecting a body motion of the user, and the predicting unit adjusts the predicted blood sugar level on the basis of a detection result of the body-motion detecting unit.

A blood sugar level during exercise shows a falling tendency. According to the seventh aspect of the invention, it is possible to detect a body motion of the user and adjust the predicted blood sugar level on the basis of a detection result. Therefore, it is possible to improve the prediction accuracy of a blood sugar level.

An eighth aspect of the invention is directed to the blood sugar level measuring device according to any of the first to seventh aspects of the invention, wherein the light-amount control unit controls, when the predicted blood sugar level is in a first range, a light amount of the measurement light using a first light amount control method and control, when the predicted blood sugar level is in second range higher than the first range, a light amount of the measurement light using a second light amount control method with power consumption smaller than power consumption in the first light amount control method.

According to the eighth aspect of the invention, when the predicted blood sugar level is in the first range, it is possible to control a light amount of the measurement light per one measurement using the first light amount control method. On the other hand, when the predicted blood sugar level is in the second range higher than the first range, it is possible to control a light amount of the measurement light per one measurement using the second light amount control method with power consumption smaller than power consumption in the first light amount control method.

A ninth aspect of the invention is directed to the blood sugar level measuring device according to the eighth aspect of the invention, wherein the blood sugar level measuring device further includes an error calculating unit configured to calculate a prediction error of the predicted blood sugar level on the basis of a blood sugar level measured by the measuring unit under the light amount control performed by the light-amount control unit using the second light amount control method, and when a predetermined condition indicating that the prediction error is relatively large is satisfied, the measuring unit measures a blood sugar level of the user again under the light amount control performed by the light-amount control unit using the first light amount control method.

According to the ninth aspect of the invention, if a prediction error is large when the second light amount control method with power consumption smaller than power consumption in the first light amount control method is used, it is possible to control a light amount of the measurement light per one measurement using the first light amount control method and measure a blood sugar level of the user again.

A tenth aspect of the invention is directed to the blood sugar level measuring device according to the eighth or ninth aspect of the invention, wherein the light amount control methods is defined by at least one of the number of light emitting elements configuring the light emitting unit, an amount of electric current supplied to the light emitting unit, an exposure time of the light emitting unit, and measurement wavelength width of the measurement light.

According to the tenth aspect of the invention, it is possible to define the light amount control methods with at least one of the number of light emitting elements configuring the light emitting unit, an amount of electric current supplied to the light emitting unit, an exposure time of the light emitting unit, and measurement wavelength width of the measurement light and control a light amount of the measurement light per one measurement.

BRIEF DESCRIPTION OF THE DRAWINGS

The invention will be described with reference to the accompanying drawings, wherein like numbers reference like elements.

FIGS. 2A and 2B are diagrams showing a configuration example of a sensor module.

FIG. 3 is a diagram showing a Clarke Error Grid scatter diagram.

FIG. 11 is a diagram showing a data configuration example of a light amount control method list.

FIG. 12 is a diagram showing a data configuration example of adjustment table for exercise time.

FIG. 14 is a diagram showing a data configuration example of a measurement result DB.

DESCRIPTION OF EXEMPLARY EMBODIMENTS

Figure 1:
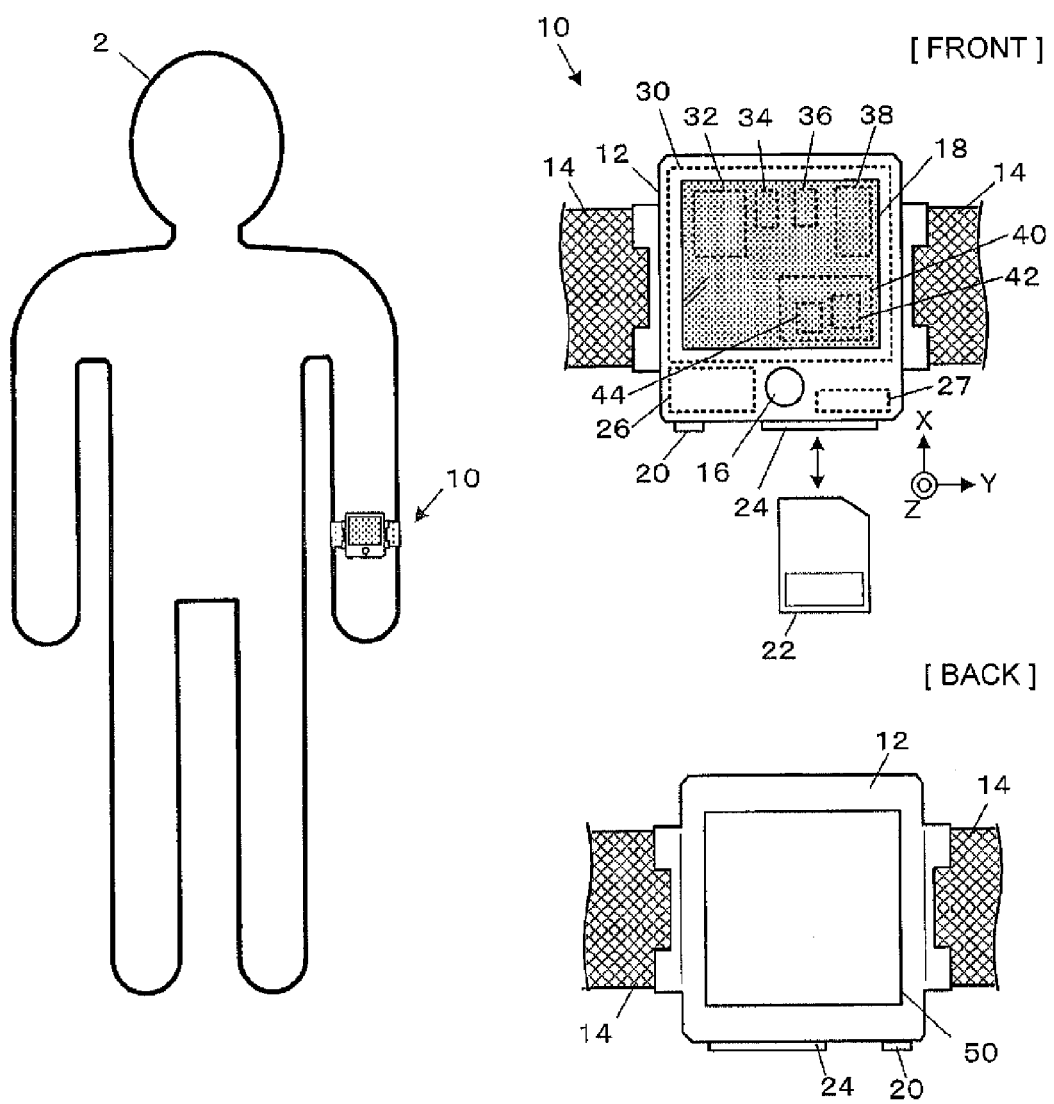
FIG. 1 is an external view showing an overall configuration example of a blood sugar level measuring device in a first embodiment.

Modes for carrying out a blood sugar level measuring device and a blood sugar level measuring method according to the invention are explained below with reference to the drawings. Note that the invention is not limited by embodiments explained below. Modes to which the invention is applicable are not limited to the embodiments. In the description of the drawings, same portions are denoted by the same reference numerals and signs.

First Embodiment

Overall Configuration

FIG. 1 is an external view showing an overall configuration example of a blood sugar level measuring device 10 of a noninvasive type in a first embodiment. The blood sugar level measuring device 10 functions as a measuring instrument that measures blood glucose concentration (so-called "blood sugar level") of a user 2 and also functions as a data logger that stores measurement data. The blood sugar level measuring device 10 can be considered a kind of a computer. As shown in FIG. 1, the blood sugar level measuring device 10 is configured as, for example, a wearable device of a wristwatch type. The blood sugar level measuring device 10 is used by being mounted and fixed to a body part such as the arm, the leg, or the neck of the user 2 by a band 14 provided in a main body case 12.

The blood sugar level measuring device 10 includes, on the front surface of the main body case 12 (a surface facing outward when the blood sugar level measuring device 10 is mounted on the user 2), as operation input means, an operation switch 16 and a touch panel 18 also functioning as image display means. The user 2 can perform various kinds of operation inputs such as measurement start operation using the operation switch 16 and the touch panel 18.

The blood sugar level measuring device 10 includes, on a side surface of the main body case 12, a communication device 20 to and from which a wired cable for communicating with an external apparatus can be attached and detached and a reader writer 24 that realizes reading and writing of data from and to a memory card 22. The blood sugar level measuring device 10 includes, on the rear surface (a surface in contact with the skin of the user 2 when the blood sugar level measuring device 10 is mounted on the user 2) side of the main body case 12, a sensor module 50 functioning as a main sensor for irradiating measurement light to the inside of a living organism of the user 2 as an irradiation wave and receiving reflected light and an acceleration sensor 27. A built-in battery 26 of a charging type and a control substrate 30 are incorporated in the inside of the main body case 12.

If the communication device 20 is configured to perform the communication with the external apparatus by radio, the communication device 20 is realized by a radio communication module and an antenna.

The memory card 22 is a nonvolatile memory of a detachable type capable of rewriting data. As the memory card 22, besides a flash memory, rewriteable nonvolatile memories such as a ferroelectric memory (FeRAM: Ferroelectric Random Access Memory) and a magnetic resistance memory (MRAM: Magnetoresistive Random Access Memory) can be used.

A charging system to the built-in battery 26 can be set as appropriate. For example, a configuration may be adopted in which an electric contact is separately provided on the rear surface side of the main body case 12 and the built-in battery 26 is set in a cradle connected to a domestic power supply and is energized and charged through the cradle via the electric contact. Wireless charging of a noncontact type may be adopted.

The acceleration sensor 27 detects an acceleration vector of the user 2. For example, the blood sugar level measuring device 10 determines an exercise state of the user 2 using, as detected acceleration, detection axis components of an X axis, a Y axis, and a Z axis of the acceleration sensor 27 inscribed in the vicinity of the main body case 12 in FIG. 1.

The control substrate 30 collectively controls the blood sugar level measuring device 10. Specifically, the control substrate 30 is mounted with a CPU (Central Processing Unit) 32, a main memory 34, a memory for measurement data 36, a touch panel controller IC (Integrated Circuit) 38, and a sensor module controller 40. Besides, electronic components such as a power supply management IC and an IC for image processing can be mounted as appropriate.

The main memory 34 is a storage medium that can store a computer program and initial setting data and store an arithmetic value of the CPU 32. The main memory 34 is realized using a RAM, a ROM, a flash memory, and the like as appropriate. Note that the computer program and the initial setting data may be stored in the memory card 22.

The memory for measurement data 36 is a data-rewritable nonvolatile memory and is a storage medium for storing measurement data of a blood sugar level. As the memory for measurement data 36, besides a flash memory, rewritable nonvolatile memories such as a ferroelectric memory (FeRAM) and a magnetic resistance memory (MRAM) can be used. Note that the measurement data may be stored in the memory card 22.

The touch panel controller IC 38 is an IC that realizes a driver function for causing the touch panel 18 to display an image and a function for realizing a touch input. The touch panel controller IC 38 and the touch panel 18 can be realized by using a publicly-known technique as appropriate.

The sensor module controller 40 includes an IC or a circuit that performs an irradiating function for measurement light by the sensor module 50 and a light receiving function for measurement light transmitted through a biological tissue of the user 2 (transmitted light) and the measurement light reflected on the biological tissue (reflected light).

More specifically, the sensor module controller 40 includes a light emitting controller unit 42 including an IC or a circuit that individually controls a plurality of light emitting elements (elements that emit measurement light through energization) included in the sensor module 50 and a light receiving controller unit 44 including an IC or a circuit that controls light reception by a plurality of light receiving elements (elements that emit electric signals corresponding to a received light amount) included in the sensor module 50.

Note that the sensor module controller 40 may be configured by a plurality of ICs. For example, the IC or the circuit equivalent to the light emission controller unit 42 and the IC or the circuit equivalent to the light reception controller unit 44 can also be configured as separate ICs. Alternatively, a part of these functions may be realized by the CPU 32.

FIGS. 2A and 2B are diagrams showing a configuration example of the sensor module 50. FIG. 2A is a front view and FIG. 2B is a sectional view. Note that, to facilitate understanding, light emitting elements 52 and light receiving elements 54 are intentionally shown large. The size, the aspect ratio, and the like of the sensor module 50 are not limited to those shown in the figures and can be set as appropriate.

The sensor module 50 is a device configured by stacking a layer in which a plurality of the light emitting elements 52 are arrayed in a plane shape and a layer in which a plurality of the light receiving elements 54 are arrayed in a plane shape. In other words, the sensor module 50 is an image sensor of a light source built-in type and is a sensor array that realizes both functions of irradiation and reception of measurement light. The sensor module 50 may be configured integrally with the sensor module controller 40.

The light emitting elements 52 are light emitting units that irradiate the measurement light and can be realized by, for example, an LED (Light Emitting Diode) or an OLED (Organic light-emitting diode). When a blood sugar level is measured, the light emitting elements 52 are elements capable of emitting light including near infrared light close to a visible region having subcutaneous transmittivity.

The light receiving elements 54 are image pickup elements that receive the transmitted light and the reflected light of the measurement light and output an electric signal corresponding to a light reception amount. The light receiving elements 54 can be realized by a semiconductor element such as a CCD (Charge Coupled Device Image Sensor) or a CMOS (Complementary Metal Oxide Semiconductor Image Sensor). One light receiving element 54 includes a plurality of elements that receive RGB wavelength components.

The sensor module 50 includes 1) a light receiving layer 51 in which the plurality of light receiving elements 54 are arrayed in a plane shape and a lattice shape, 2) a light blocking layer 53 that selectively blocks lights other than lights traveling to the light receiving elements 54, 3) a spectral layer 55 that selectively transmits near infrared light, and 4) a light emitting layer 57 in which the plurality of light emitting elements 52 are arrayed in a plane shape and a lattice shape between light receiving elements adjacent to each other in positions where the light emitting elements 52 do not hinder an optical path of the lights transmitted through and reflected on the biological tissue and reaching the light receiving elements 54. The light receiving layer 51, the light blocking layer 53, the spectral layer 55, and the light emitting layer 57 are stacked in order from a base side (the front side of the main body case 12).

Like a publicly-known CCD image sensor, the light receiving elements 54 of the light receiving layer 51 are arranged in a matrix shape in which pixels can be identified in an Xs-Ys rectangular coordinate system. That is, the sensor module 50 functions in the same manner as the publicly-known image sensor. Note that the shape, the size, and the arrangement pattern of the light receiving elements 54 can be set as appropriate.

The light emitting elements 52 of the light emitting layer 57 are arranged one by one in a butting portion of corners of the light receiving elements 54 in the vicinity when the sensor module 50 is viewed from the front (the rear side of the main body case 12). More specifically, one light emitting element 52 is arranged in a butting portion of corners of four light receiving elements 54. All the light emitting elements 52 are arranged in a matrix shape in which the light emitting elements 52 can be identified in an Xs-Ys rectangular coordinate system same as that of the light receiving elements 54. The sensor module 50 includes a driving mechanism that causes the light emitting elements 52 to selectively emit light. For example, the light emitting elements 52 can be drive-controlled in the same manner as an active matrix system of a liquid crystal panel display.

For manufacturing of the sensor module 50 having such a stacked structure, a semiconductor microfabrication technique used for manufacturing of the publicly-known CCD image sensor and an OLED display can be applied as appropriate.

Note that the size and the arrangement interval of the light emitting elements 52, the size and the arrangement interval of the light receiving elements 54, and the like can be set as appropriate. For example, the arrangement intervals are suitably set to 1 to 500 [μm] and can be set to, for example, about 50 to 200 [μm] according to a balance between manufacturing costs and measurement accuracy. In the sensor module 50, a condensing layer including a further optical element can be provided for the purpose of narrowing an irradiation range of the measurement light irradiated by the light emission of the light emitting elements 52 and deflecting the measurement light or accurately collecting, in the light receiving elements 54, the lights transmitted through and reflected on the biological tissue. A protection layer or the like that prevents damage to the surface of the sensor module 50 may be provided as appropriate. The sensor module 50 is not limited to the configuration in which the light emitting elements 52 and the light receiving elements 54 are stacked. The light emitting elements 52 and the light receiving elements 54 may be placed side by side.

Overview

In the first embodiment, a blood sugar level of the user 2 is predicted (the predicted blood sugar level is hereinafter referred to as "predicted blood sugar level") on the basis of a measurement value of a blood sugar level measured in the past (hereinafter referred to "measured blood sugar level" as appropriate). A light amount per one measurement, more specifically, an overall amount of light amounts of the light emitting elements 52 caused to emit lights in one measurement is controlled on the basis of the predicted blood sugar level to measure a blood sugar level. The control of the light amount is performed by selectively applying a different plurality of light amount control methods.

If the light amount per one measurement is not limited, a blood sugar level can be measured at highest accuracy. On the other hand, if the light amount per one measurement is reduced, although the measurement accuracy is deteriorated because of a factor such as a decrease in an S/N ratio, power consumption can be suppressed.

As a method of evaluating an allowable error of a measurement value with respect to a true value of a blood sugar level, a method called Clarke Error Grid analysis is known. FIG. 3 is a diagram showing a Clarke Error Grid scatter diagram. In general, in a hypoglycemia state, high measurement accuracy is requested and an allowable error of a measurement value is small. In other words, when a blood sugar level is high, requested measurement accuracy is relaxed compared with when a blood sugar level is low. For example, in the Clarke Error Grid analysis, if a relation between a true value and a measurement value belongs to an A zone in the scatter diagram shown in FIG. 3, it is considered that there is clinically sufficient measurement accuracy. However, an error range of the A zone narrows as the true value decreases. As a specific numerical value, if an error rate of the measurement value with respect to the true value is generally within ±20%, it is considered that the relation belongs to the A zone.

Therefore, in the first embodiment, two kinds of light amount control methods, i.e., a first light amount control method and a second light amount control method are defined beforehand according to the number of the light emitting elements 52 caused to emit lights in measurement (the number of light emitting positions (light emitting elements for measurement 52-1) explained below; hereinafter referred to as "number of light emitting elements"). Specifically, the number of light emitting elements of the second light amount control method is defined as a number smaller than the number of light emitting elements of the first light amount control method. However, in both the light amount control methods, the number of light emitting elements is defined on the basis of a number with which required measurement accuracy can be realized.

When the predicted blood sugar level is low, the first light amount control method is applied to realize high measurement accuracy. On the other hand, when the predicted blood sugar level is high, the second light amount control method with small power consumption is applied to reduce power consumption while securing requested measurement accuracy.

Prior to measurement, the blood sugar level measuring device 10 is fixed by the band 14 to cause the rear surface, on which the sensor module 50 is exposed, to adhere to the skin of the user 2. By causing the sensor module 50 to adhere to the skin, it is possible to suppress factors of deterioration in measurement accuracy such as reflection of the measurement light on the skin surface and scattering of the measurement light in a tissue near the skin surface.

As a measurement procedure for a blood sugar level, first, a blood vessel present under the skin of a body covered with the sensor module 50 is selected. Irradiation and reception of the measurement light are performed targeting the selected blood vessel. Thereafter, a blood vessel transmitted light component transmitted through the blood vessel is extracted from a light reception result (intensity of received light). A blood sugar level is calculated from a relative spectrum (a light absorption spectrum) that reflects an amount of the blood vessel transmitted light component.

Figure 4:
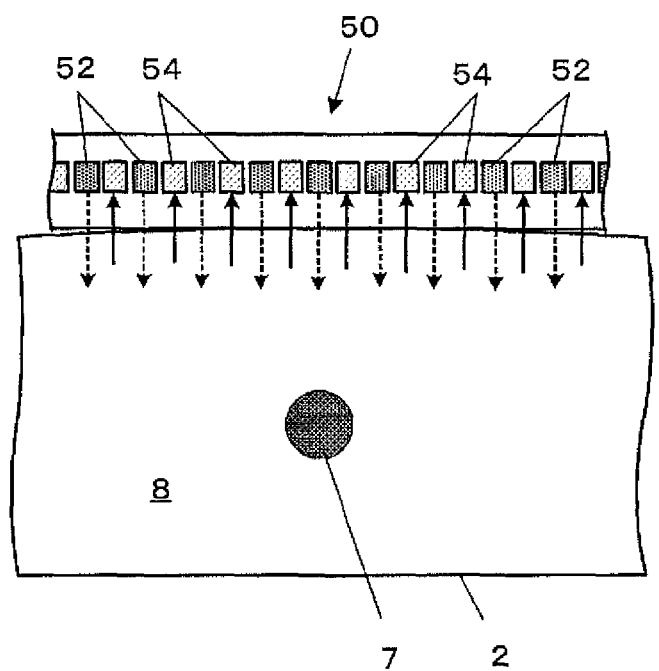
FIG. 4 is a conceptual diagram showing an acquisition method for a blood vessel position.

To select a blood vessel, it is necessary to grasp where under the skin covered with the sensor module 50 the blood vessel is present. FIG. 4 is a conceptual diagram showing an acquisition method for a blood vessel position and is equivalent to a sectional view of a portion of the user 2 covered with the sensor module 50. Note that the sensor module 50 is shown in a simplified form.

In acquisition of a blood vessel position, first, in the same manner as vein pattern detection in a publicly-known vein authentication technique, the light emitting elements 52 included in the sensor module 50 are caused to emit lights all at once to irradiate the measurement light to an entire mounted part of the sensor module 50. Lights transmitted through and reflected on a biological tissue under the skin (a subcutaneous tissue) are received (photographed) by using all the right receiving elements 54 to acquire a biological image.

The biological image acquired by the sensor module is a set of luminance data of pixels respectively corresponding to the light receiving elements 54 of the sensor module 50 and is obtained as a two-dimensional image of an Xs-Ys rectangular coordinate system same as a pixel coordinate of the sensor module 50. Because of the influence of blood flowing on the inside of the blood vessel, the blood vessel absorbs near infrared light more than a place where a blood vessel 7 is absent. Therefore, the blood vessel position has lower luminance than a region other than the blood vessel position. Therefore, by extracting a region where luminance is low in the biological image, it is possible to identify, for each of the pixels, whether the blood vessel is in a photograph, in other words, whether the blood vessel is present under the light receiving elements 54. "Under the light receiving elements 54" is an expression suitable for operation explanation of the device for the user 2. More accurately, "under the light receiving elements 54" means an opposed direction of the light receiving elements 54 across the skin surface (a direction in which light is received).

Figure 5:
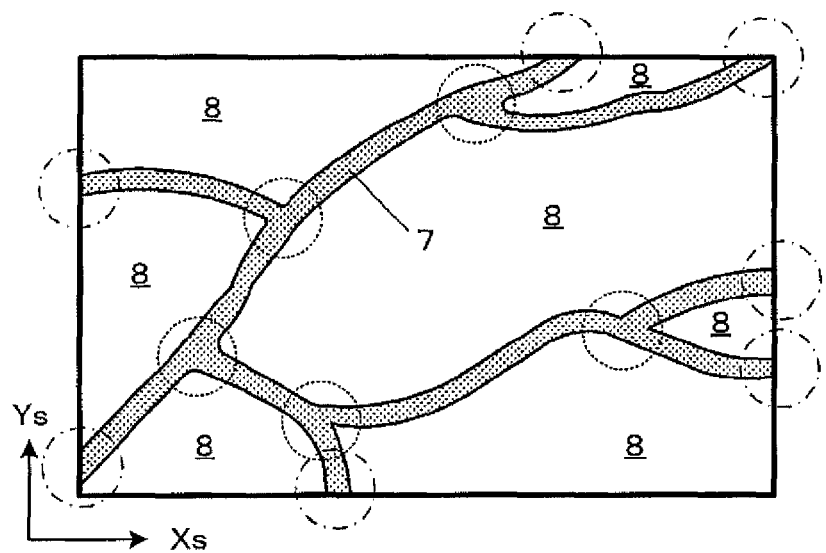
FIG. 5 is a diagram schematically showing a biological image.

FIG. 5 is a diagram schematically showing the biological image. In an example shown in FIG. 5, a belt-like region hatched by oblique lines or dot patterns indicates the position of the vessel 7. White void parts indicate biological tissue portions (non-blood vessel sections) 8 where the blood vessel 7 is absent under the skin. Note that the acquisition method for a blood vessel position is not limited to the illustrated method. For example, it is also conceivable adopt a method of acquiring a relative position of a biological inner structure beforehand using a publicly-known biological tomographic image measuring technique such as ultrasonic echo or MRI (Magnetic Resonance Imaging), or CT (Computed Tomography) and determining a blood vessel position on the basis of the relative position.

Figure 6:
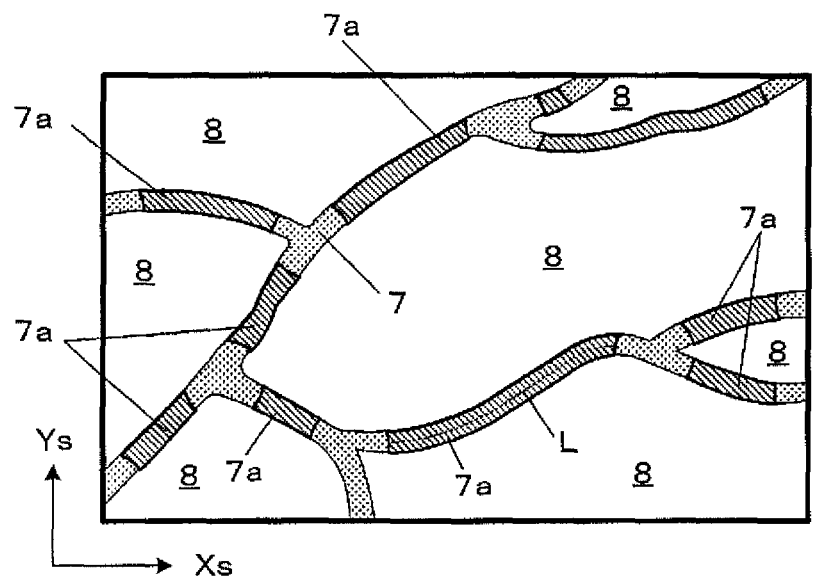
FIG. 6 is a diagram showing a blood vessel portion obtained by excluding an accuracy deterioration factor region from a blood vessel position shown in FIG. 5.

If the position of the vessel 7 is acquired, a blood vessel portion suitable for measurement is selected as a measurement target region. First, blood vessel portions such as branching points and merging points of the blood vessel 7 indicated by broken line circles and biological image end portions indicated by alternate long and short dash line circles in FIG. 5 are excluded as portions that could be factors of deterioration in measurement accuracy (accuracy deterioration factor portions). This is because, if the measurement light reaches the branching points and the merging points of the blood vessel, it is likely that transmitted light and reflected light of the non-blood vessel sections 8 other than the blood vessel are mixed in received light in a light receiving position and the mixed light affects a light absorption spectrum of blood vessel transmitted light, which is originally desired to be obtained, and deteriorates the measurement accuracy. Blood vessel portions of the biological image end portions indicated by the alternate long and short dash line circles are excluded because it is likely that branching points and merging points of the blood vessel are present in the vicinity of the outer side of a photographing range. FIG. 6 a diagram showing an example of blood vessel portions 7a obtained by excluding the accuracy deterioration factor portions from the blood vessel position shown in FIG. 5. For example, hatched portions of oblique lines are the blood vessel portions 7a remaining without being excluded.

Figure 7:
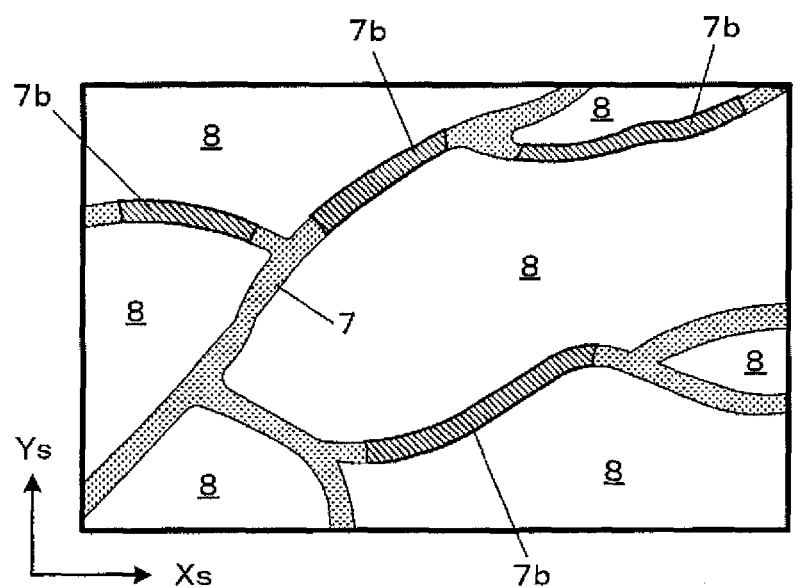
FIG. 7 is a diagram showing a blood vessel portion selected on the basis of minimum region length.

Irradiated lights from the light emitting elements 52 are diffused and reflected in the biological tissue. A part of the irradiated lights is received by the light receiving elements 54. That is, a part of the lights received by the light receiving elements 54 changes to blood vessel transmitted light. As a ratio of the blood vessel transmitted light is higher, it is possible to obtain a light absorption spectrum more conspicuously representing characteristics of components in the blood. Therefore, the measurement accuracy is higher. A relatively thin blood vessel is extracted thin in a blood vessel pattern specified from the biological image. In some case, for example, the thin blood vessel is discontinuously extracted. A blood vessel present in a relatively deep position is also discontinuously extracted because a light amount of the blood vessel transmitted light is small. Therefore, a blood vessel portion having length equal to or larger than predetermined minimum region length is selected and set as a measurement target region. The length of the blood vessel portion may be set to, for example, the length of a center line L of the blood vessel portion or may be set to the number of pixels configuring the center line L. FIG. 7 is a diagram showing an example of finally selected blood vessel portions 7b. For example, the blood vessel portions 7b indicated by hatching of oblique lines are selected on the basis of "minimum region length".

If the blood vessel portions 7b suitable for measurement are selected as measurement target regions, a light emitting position (a light emitting element for measurement) of the measurement light, a light receiving position (a light receiving element for measurement) appropriate for obtaining blood vessel transmitted light (transmitted light of the blood vessel portions 7b), and a light receiving position (a light receiving element for reference) appropriate for obtaining transmitted light for reference are selected. The transmitted light for reference means light not transmitted through the blood vessel portions 7b and transmitted through only the non-blood vessel sections 8 in the vicinity of the blood vessel portions 7b.

Figure 8:
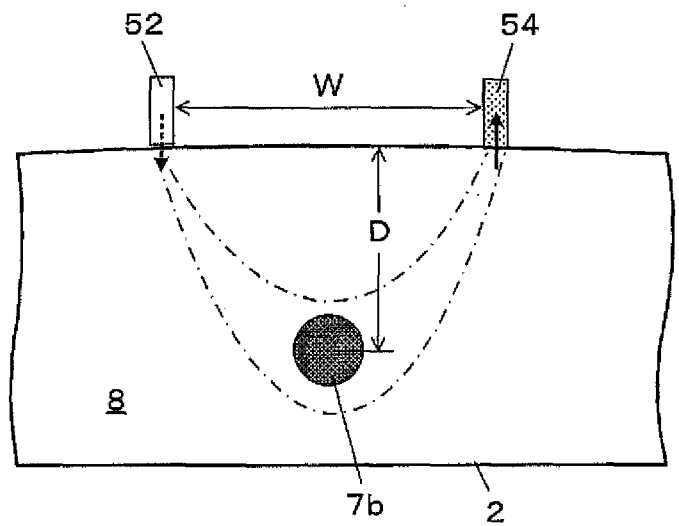
FIG. 8 is a diagram for explaining propagation of light in a biological tissue.

FIG. 8 is a diagram for explaining propagation of light in the biological tissue. A sectional view taken along the depth direction is shown. Measurement light irradiated from a certain light emitting element 52 is diffused and reflected in the biological tissue. A part of the irradiated measurement light reaches the light receiving element 54. A propagation route of the light is formed in a so-called banana shape (a region between two arcs). Width in the depth direction is the largest substantially near the center. The depth (reachable depth) of the propagation route is smaller as the interval between the light emitting element 52 and the light receiving element 54 is smaller. The depth is larger as the interval is larger.

To improve the measurement accuracy, it is desirable that more blood vessel transmitted light is received by the light receiving element 54. Therefore, an optimum interval (an optimum distance) W between the light emitting element 52 and the light receiving element 54 can be set according to assumed depth (the distance from the skin surface to the blood vessel center) D of the blood vessel 7 on the premise that the blood vessel 7 is located substantially in the center between the light emitting element 52 and the light receiving element 54. The optimum distance W is a distance about two times as large as the depth D of the blood vessel 7. For example, when the depth D is about 3 mm, the optimum distance W is about 5 to 6 mm.

Therefore, a first relative position condition is set as "the blood vessel 7 is located in the center portion between the light emitting position and the light receiving position for measurement and the distance between the light emitting position and the light receiving position for measurement is equal to the predetermined optimum distance W". The light emitting element 52 and the light receiving element satisfying the first relative position condition are searched and selected as the light emitting position and the light receiving position for measurement. In addition, a second relative position condition is set as "the blood vessel 7 is absent between the light emitting position and the light receiving position for reference and the distance between the light emitting position and the light receiving position for reference is equal to the predetermined optimum distance W". The light receiving element 54 satisfying the second relative position condition is selected as the light receiving position for reference.

Figure 9:
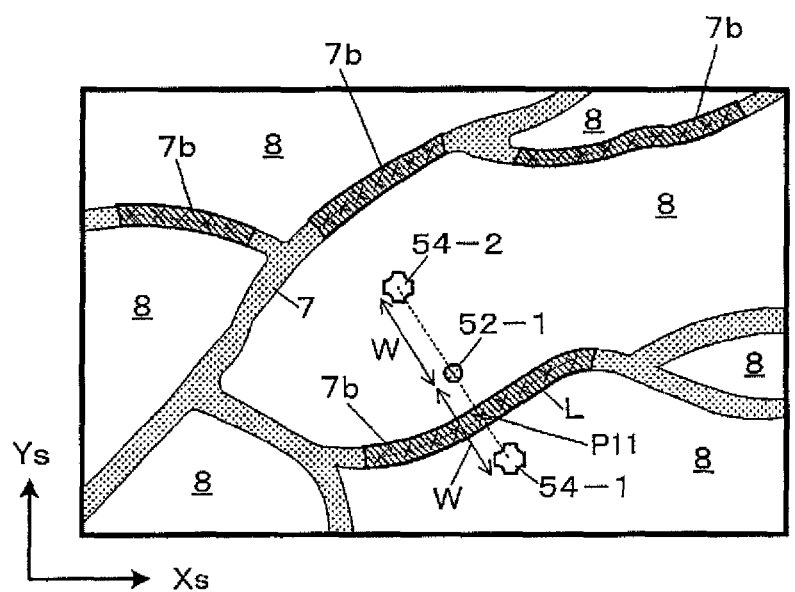
FIG. 9 is a diagram for explaining measurement point candidate setting processing.

Actually, the light emitting position, the light receiving position for measurement, and the light receiving position for reference are selected for each of a plurality of measurement point candidates (measurement point candidate setting processing). FIG. 9 is a diagram for explaining the measurement point candidate setting processing. In the measurement point candidate setting processing, for example, as indicated by "x" marks in FIG. 9, measurement point candidates are set at a predetermined interval on the center lines L of the blood vessel portions 7b. A combination of the light emitting element 52 and the light receiving element 54 satisfying the first relative position condition and satisfying the second relative position condition is searched for each of the measurement point candidates. For example, if attention is paid to one measurement point candidate P11, the light emitting element 52 and the light receiving element 54, in the center portion between which the measurement point candidate P11 is located and the distance between which is the optimum distance W, are respectively set as a light emitting element for measurement 52-1 and a light receiving element for measurement 54-1 to select the light emitting position and the light receiving position for measurement. The light receiving position for reference is selected on an extended line connecting the light emitting position and the light receiving position for measurement and on the opposite side of the light receiving position for measurement when viewed from the light emitting position. The light receiving position for reference is set as a light receiving element for reference 54-2. It is assumed that all of the light emitting position, the light receiving position for measurement, and the light receiving position for reference are not located on the blood vessel 7 (are located on the non-blood vessel sections 8). Concerning the other measurement point candidates, the light emitting position, the light receiving position for measurement, and the light receiving position for reference are selected in the same manner. Note that, if the combination of the light emitting element 52 and the light receiving element 54 satisfying the first relative position condition and satisfying the second relative position condition is absent, the measurement point candidate corresponding to the light emitting position, the light receiving position for measurement, and the light receiving position for reference is deleted.

If the light emitting position, the light receiving position for measurement, and the light receiving position for reference are selected for each of the plurality of measurement point candidates as explained above, a blood sugar level of the user 2 is predicted. The first light amount control method or the second light amount control method is selectively applied on the basis of the predicted blood sugar level to determine the number of light emitting elements and select measurement point candidates equivalent to the determined number of light emitting elements as measurement points.

Subsequently, the light emitting positions (the light emitting elements for measurement 52-1) at all the measurement points are caused to emit lights to irradiate the measurement light. The blood vessel transmitted light component is extracted for each of the measurement points from light reception results in the light receiving positions for measurement (the light receiving elements for measurement 54-1) and the light receiving positions for reference (the light receiving elements for reference 54-2) corresponding to the light emitting positions. For example, a wavelength λ of the measurement light is changed in a near infrared region by causing each of the light emitting elements for measurements 52-1 to emit light while shifting light emission wavelength thereof by predetermined measurement wavelength at a time. Transmittance T(λ) of the blood vessel transmitted light is calculated for each wavelength λ concerning each of the measurement points. Note that a configuration in which the wavelength λ of the measurement light is changed is not limited to the configuration in which the light emission wavelength of the light emitting element for measurement 52-1 is shifted by predetermined measurement wavelength width at a time. The wavelength λ of the measurement light may be changed by changing transmission band width of a spectral filter for each predetermined measurement wavelength width.

The transmittance T(λ) at the measurement points can be calculated from light intensity Os(λ) obtained by the light receiving element 54 for measurement and light intensity Or(λ) obtained by the light receiving element 54 for reference according to the following Expression (1). Light absorptivity is calculated from the calculated transmittance T(λ) and a light absorption vector is generated.

$$T(\lambda)=Os(\lambda)/Or(\lambda) \tag{1}$$

Thereafter, a blood sugar level is calculated (estimated) from the light absorption spectrum using a "calibration curve" indicating a relation between blood glucose concentration and light absorbance set in advance. Note that concerning a method of generating a light absorption spectrum and calculating a blood sugar level, a publicly-known technique can be adopted as appropriate.

Functional Configuration

Figure 10:
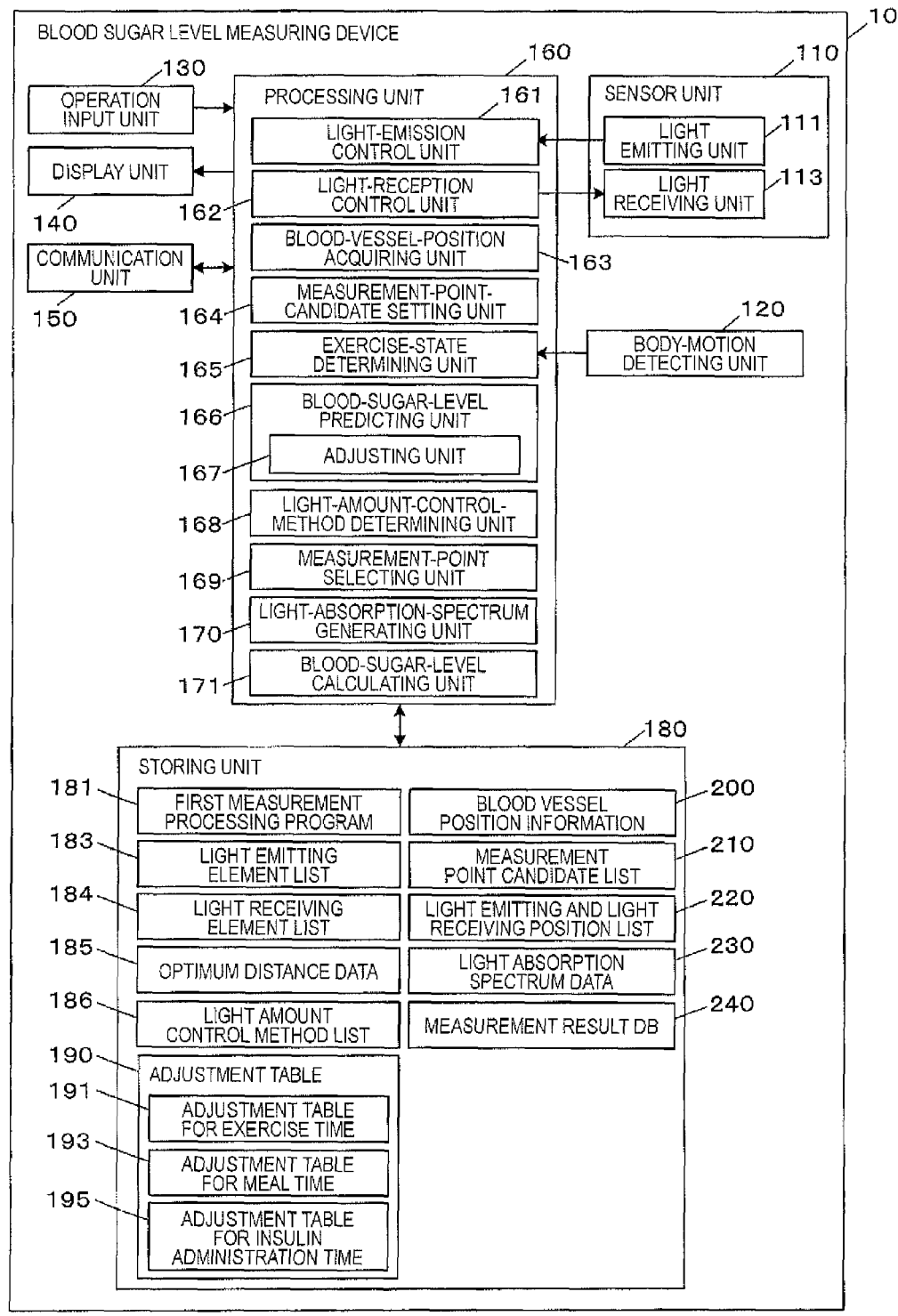
FIG. 10 is a block diagram showing a functional configuration example of the blood sugar level measuring device in the first embodiment.

FIG. 10 is a block diagram showing a main functional configuration example of the blood sugar level measuring device 10 in the first embodiment. As shown in FIG. 10, the blood sugar level measuring device 10 includes a sensor unit 110, a body-motion detecting unit 120, an operation input unit 130, a display unit 140, a communication unit 150, a processing unit 160, and a storing unit 180.

The sensor unit 110 corresponds to the sensor module 50 shown in FIGS. 2A and 2B. The sensor unit 110 includes a light emitting unit 111 configured by the plurality of light emitting elements 52 and a light receiving unit 113 configured by the plurality of light receiving elements 54. Arrangement positions (Xs-Ys coordinate values) of the light emitting elements 52 configuring the light emitting unit 111 are stored in the storing unit 180 in advance as a light emitting element list 183 in which the arrangement positions are associated with light emitting element numbers allocated to the relevant light emitting elements 52. Arrangement positions (Xs-Ys coordinate values) of the light receiving elements 54 configuring the light receiving unit 113 are stored in the storing unit 180 in advance as a light receiving element list 184 in which the arrangement positions are associated with light receiving element numbers allocated to the relevant light receiving elements 54.

The body-motion detecting unit 120 is a unit for detecting a body motion. For example, the body-motion detecting unit 120 can be realized using a MEMS (Micro Electro Mechanical Systems) sensor. The acceleration sensor 27 shown in FIG. 1 corresponds to the body-motion detecting unit 120. The body-motion detecting unit 120 outputs detected acceleration to the processing unit 160 at any time.

The operation input unit 130 is realized by various switches such as a button switch and a dial switch and an input device such as a touch panel. The operation input unit 130 outputs an operation input signal to the processing unit 160 according to various operation inputs performed by the user 2. The operation switch 16 and the touch panel 18 shown in FIG. 1 correspond to the operation input unit 130.

The display unit 140 is realized by a display device such as an LCD (Liquid Crystal Display) or an EL display (Electraluminescence display). The display unit 140 displays various screens on the basis of a display signal input from the processing unit 160. The touch panel 18 shown in FIG. 1 corresponds to the display unit 140.

The communication unit 150 is a communication device for transmitting and receiving information used inside the device between the communication unit 150 and an external information processing apparatus under the control by the processing unit 160. The communication device 20 shown in FIG. 1 corresponds to the communication unit 150. As a communication system of the communication unit 150, it is possible to adopt various systems such as a form of connecting the communication unit 150 by wire via a cable conforming to a predetermined communication standard, a form of connecting the communication unit 150 to a charger called cradle via an intermediate device, and a form of connecting the communication unit 150 by radio using radio communication.

The processing unit 160 is realized by a microprocessor such as a CPU (Central Processing Unit) or a DSP (Digital Signal Processor) and a control device and an arithmetic device such as an ASIC (Application Specific Integrated Circuit). The processing unit 160 collectively controls the units of the blood sugar level measuring device 10. The control substrate 30 shown in FIG. 1 corresponds to the processing unit 160. The processing unit 160 includes a light-emission control unit 161, a light-reception control unit 162, a blood-vessel-position acquiring unit 163, a measurement-point-candidate setting unit 164, an exercise-state determining unit 165, a blood-sugar-level predicting unit 166 functioning as a predicting unit, a light-amount-control-method determining unit 168, a measurement-point selecting unit 169, a light-absorption-spectrum generating unit 170, and a blood-sugar-level calculating unit 171. Note that the units configuring the processing unit 160 may be configured by hardware such as a dedicated module circuit.

The light-emission control unit 161 individually controls light emission of the light emitting elements 52 configuring the light emitting unit 111. For example, the light-emission control unit 161 can be realized by using a driving control technique of a so-called active matrix system. The light-emission control unit 161 functions as alight-amount control unit together with the measurement-point-candidate setting unit 164, the light-amount-control-method determining unit 168, and the measurement-point selecting unit 169.

The light-reception control unit 162 performs control for reading out, from received light received by the light receiving elements 54 of the light receiving unit 113, an electric signal corresponding to the intensity of the received light. The light-reception control unit 162 functions as a measuring unit together with the light-absorption-spectrum generating unit 170 and the blood-sugar-level calculating unit 171.

The blood-vessel-position acquiring unit 163 acquires a biological image under the skin covered with the sensor module 50 (see FIG. 5), processes the biological image to acquire a blood vessel position, and selects a blood vessel portion suitable for measurement as a measurement target region. The acquisition of the blood vessel position is realized by using, as appropriate, a photographing technique for a biological image in a publicly-known vein authentication technique or the like or a technique for identifying a vein pattern from a biological image in the publicly-known vein authentication technique or the like.

The measurement-point-candidate setting unit 164 is a functional unit that performs measurement point candidate setting processing. The measurement-point-candidate setting unit 164 sets a plurality of measurement point candidates along the blood vessel portion set as the measurement target region. In this case, the measurement-point-candidate setting unit 164 searches for a combination of the light emitting element 52 and the light receiving element 54 satisfying the first relative position condition and satisfying the second relative position condition to select, for each of the measurement point candidates, the light emitting position (the light emitting element for measurement 52-1), the light receiving position for measurement (the light receiving element for measurement 54-1), and the light receiving position for referenced (the light receiving element for reference 54-2) in advance. The optimum distance W is stored in the storing unit 180 in advance as optimum distance data 185.

The exercise-state determining unit 165 calculates exercise intensity on the basis of the detected acceleration input from the body-motion detecting unit 120 and determines an exercise state of the user 2 (whether the user 2 is performing exercise).

The blood-sugar-level predicting unit 166 predicts a blood sugar level of the user 2 on the basis of a measured blood sugar level in the past. The blood-sugar-level predicting unit 166 includes an adjusting unit 167 that adjusts the predicted blood sugar level on the basis of the exercise intensity of the user 2 and meal information and insulin administration information acquired by receiving an operation input of the user 2.

The light-amount-control-method determining unit 168 selectively applies the first light amount control method or the second light amount control method on the basis of the predicted blood sugar level and determines the number of light emitting elements.

The measurement-point selecting unit 169 selects, as measurement points, measurement point candidates equivalent to the number of light emitting elements out of the measurement point candidates.

The light-absorption-spectrum generating unit 170 causes the light emitting elements for measurement 52-1 at all the measurement points to irradiate measurement light under the control by the light-emission control unit 161 and the light-reception control unit 162. The light-absorption-spectrum generating unit 170 generates a light absorption spectrum on the basis of light reception results of the light receiving elements for measurement 54-1 and the light receiving elements for reference 54-2 at all the measurement points.

The blood-sugar-level calculating unit 171 calculates a blood sugar level on the basis of the light absorption spectrum. For example, the blood-sugar-level calculating unit 171 calculates a blood sugar level from the light absorption spectrum using an analysis method such as a multiple regression analysis method, a main component regression analysis method, a PLS regression analysis method, or an independent component analysis method.

The storing unit 180 is realized by various IC (Integrated Circuit) memories such as a ROM (Read Only Memory), a flash ROM, and a RAM (Random Access Memory) or a storage medium such as a hard disk. The storing unit 180 stores in advance or temporarily stores every time processing is performed a computer program for causing the blood sugar level measuring device 10 to operate and realizing various functions included in the blood sugar level measuring device 10, data used during execution of the computer program, and the like. In FIG. 1, the main memory 34 and the memory for measurement data 36 mounted on the control substrate 30 and the memory card 22 correspond to the storing unit 180.

The storing unit 180 stores in advance a first measurement processing program 181 for causing the processing unit 160 to function as the light-emission control unit 161, the light-reception control unit 162, the blood-vessel-position acquiring unit 163, the measurement-point-candidate setting unit 164, the exercise-state determining unit 165, the blood-sugar-level predicting unit 166, the light-amount-control-method determining unit 168, the measurement-point selecting unit 169, the light-absorption-spectrum generating unit 170, and the blood-sugar-level calculating unit 171 and performing first measurement processing (see FIG. 15), a light emitting element list 183, a light receiving element list 184, optimum distance data 185, a light amount control method list 186, and an adjustment table 190. Further, the storing unit 180 stores, according to implementation of measurement, blood vessel position information 200, a measurement point candidate list 210, a light emitting and light receiving position list 220, light absorption spectrum data 230, and a measurement result DB 240.

The light amount control method list 186 stores a list of light amount control methods selectively applied on the basis of the predicted blood sugar level of the user 2. FIG. 11 is a diagram showing a data configuration example of the light amount control method list 186. As shown in FIG. 11, in the light amount control method list 186, the number of light emitting elements $D_{21}$ of the first light amount control method applied when the predicted blood sugar level is smaller than a predetermined threshold set as a first range in advance and the number of light emitting elements $D_{23}$ of the second light amount control method applied with the predicted blood sugar level is equal to or larger than a predetermined threshold set as a second range are set. Specific values of the numbers of light emitting elements $D_{21}$ and $D_{23}$ are defined in advance according to the procedure explained above. However, at least the number of light emitting elements $D_{23}$ is set as a number smaller than the number of light emitting elements $D_{21}$.

The adjustment table 190 includes adjustment tables 191, 193, and 195 for exercise time, for meal time, and insulin administration time. In all the adjustment tables 191, 193, and 195, for each of adjustment conditions, adjustment amounts corresponding to the adjustment condition are set.

FIG. 12 is a diagram showing a data configuration example of the adjustment table for exercise time 191. As shown in FIG. 12, the adjustment table for exercise time 191 is a data table in which adjustment conditions and adjustment amounts are associated. In the adjustment conditions, degrees of exercise states represented by ranges of exercise intensity and duration of the exercise are set stepwise. On the other hand, in the adjustment amounts, falling widths of a blood sugar level at every measurement interval (in the first embodiment, 1 minute) assumed according to the degrees of the exercise states corresponding to the adjustment amounts are set. This is because, although a blood sugar level during exercise shows a falling tendency, a falling amount of the blood sugar level fluctuates according to a degree of an exercise state. In the prediction of a blood sugar level, when the exercise-state determining unit 165 determines that the exercise state is "exercising", the adjusting unit 167 specifies a degree of an exercise state of the user 2 according to which adjustment condition set in the adjustment table for exercise time 191 is satisfied. The adjustment unit 167 adjusts the predicted blood sugar level using an adjustment amount corresponding to the degree of the exercise state. Consequently, it is possible to improve prediction accuracy of a blood sugar level.

In the adjustment table for meal time 193, a plurality of meal menus are registered as adjustment conditions. Adjustment amounts corresponding to the respective meal menus (dietary contents) are set. This is because, although a blood sugar level during a meal shows a rising tendency, a rising amount of the blood sugar level fluctuates according to a meal menu. In predicting a blood sugar level, the adjusting unit 167 determines that a predetermined period (e.g., 30 minutes) from the start of a meal is meal time. When determining that it is the meal time, the adjusting unit 167 adjusts the predicted blood sugar level with an adjustment amount corresponding to a meal menu of the user 2 set in the adjustment table for meal time 193. Consequently, it is possible to improve the prediction accuracy of a blood sugar level.

In an adjustment table for insulin administration time 195, adjustment amounts, an adjustment condition of which is administration of insulin, is set. This is because a blood sugar level falls after the insulin administration. In predicting a blood sugar level, the adjusting section 167 determines that a predetermined period (e.g., 3 minutes) from administration of insulin is insulin administration time. When determining that it is the insulin administration time, the adjusting unit 167 adjusts the predicted blood sugar level with an adjustment amount set in the adjustment table for insulin administration time 195. Consequently, it is possible to improve the prediction accuracy of a blood sugar level.

Note that the adjustment tables 191, 193, and 195 may be used as tables common to all users or may be prepared for each of the users. During exercise, during a meal, and during insulin administration, there is an individual difference in blood sugar level fluctuation. Therefore, if the blood sugar level fluctuation is analyzed from a measured blood sugar level of a user in the past and an adjustment amount is set for the user, it is possible to further improve the prediction accuracy of a blood sugar level.

Figure 13:
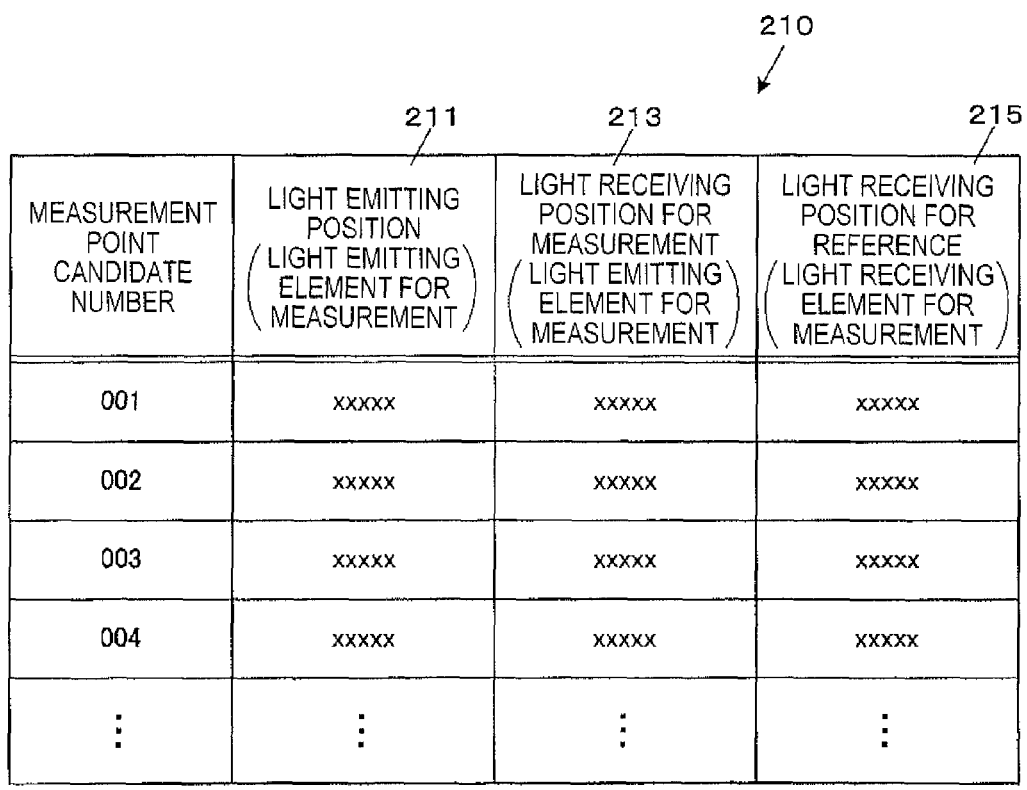
FIG. 13 is a diagram showing a data configuration example of a measurement point candidate list.

The measurement point candidate list 210 stores the light emitting position, the light receiving position for measurement, and the light receiving position for reference selected as a result of the measurement point candidate setting processing. FIG. 13 is a diagram showing a data configuration example of the measurement point candidate list 210. As shown in FIG. 13, the measurement point candidate list 210 is a data table in which, in association with a measurement point candidate number, a light emitting position 211, a light receiving position for measurement 213, a light emitting position for reference 215 selected concerning a measurement point candidate corresponding to the measurement point candidate number are set. In the light emitting position 211, light receiving element numbers of the light emitting elements 52 corresponding thereto, that is, the light emitting elements for measurement 52-1 are registered. In the light receiving position for measurement 213, light receiving element numbers of the light receiving elements 54 corresponding thereto, that is, the light receiving elements for measurement 54-1 are registered. In the light receiving position for reference 215, light receiving element numbers of the light receiving elements 54 corresponding thereto, that is, the light receiving elements for reference 54-2 are registered.

The measurement result DB 240 accumulates and stores measurement results of blood sugar levels of the user 2 performed to the present. FIG. 14 is a diagram showing a data configuration example of the measurement result DB 240. In the measurement result DB 240, measurement result data in which measurement date and time, a measured blood sugar level, exercise intensity, meal information, and insulin administration information are associated is generated and added every time measurement is performed once. The meal information is set when an operation input of the user 2 is performed in measuring a measured blood sugar vale corresponding to the meal information. If an operation input indicating that a meal is started is performed, a circle mark is set and dietary content input by operation is set. Concerning the operation input of the dietary content, the meal menus registered in the adjustment table for meal time 193 are displayed as a list. The operation input is received by selection operation from the list. Similarly, the insulin administration information is set when an operation input of the user 2 is performed in measuring a measured blood sugar level corresponding to the insulin administration information. If an operation input indicating that insulin is administered is performed, a circle mark is set.

Flow of Processing

Figure 15:
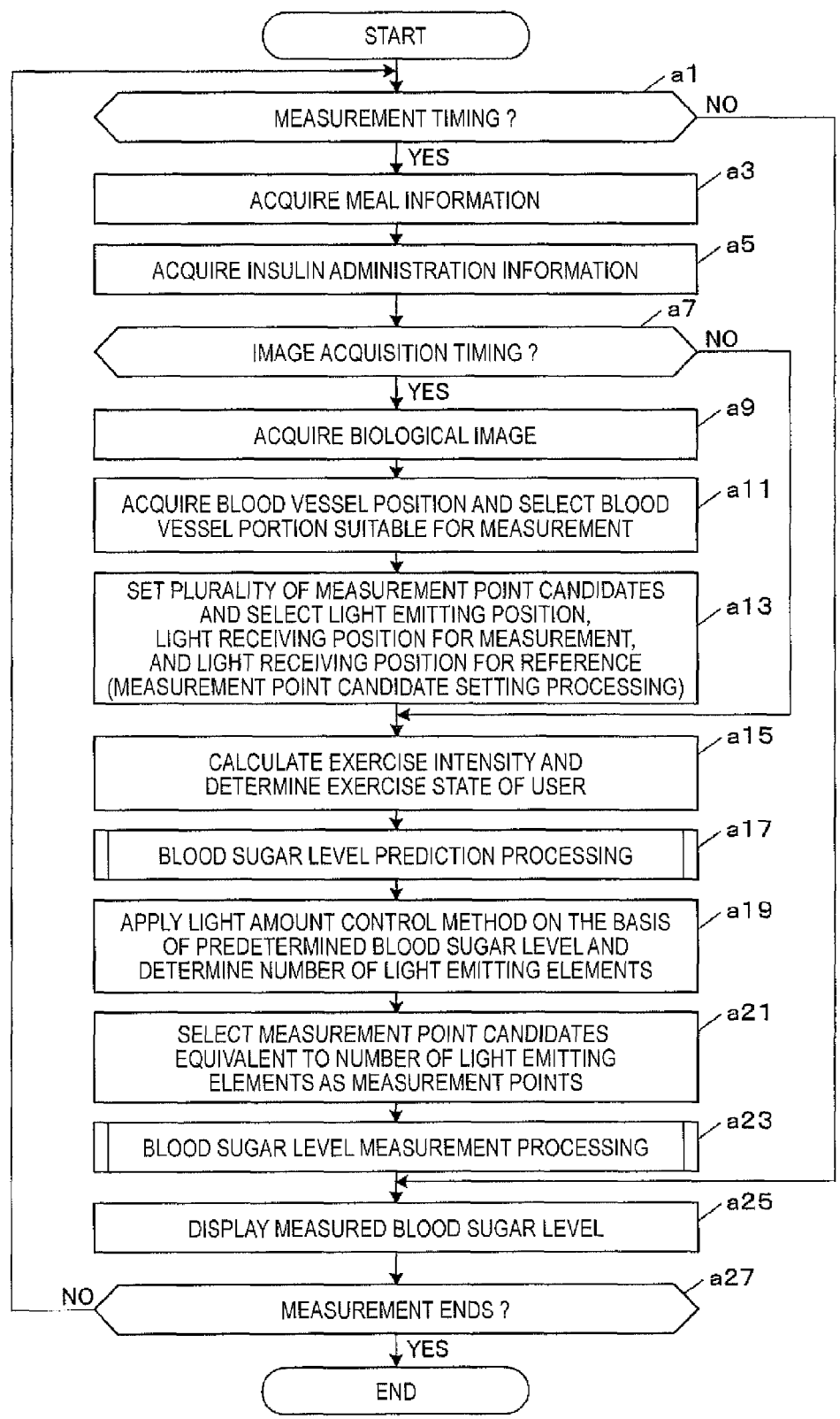
FIG. 15 is a flowchart for explaining a processing procedure of first measurement processing.

FIG. 15 is a flowchart for explaining a processing procedure of first measurement processing. Note that the processing explained below can be realized by the processing unit 160 reading out the first measurement processing program 181 from the storing unit 180 and executing the first measurement processing program 181. The first measurement processing is started when the blood sugar level measuring device 10 is mounted on the body of the user 2 and predetermined measurement start operation is input.

As shown in FIG. 15, in the first measurement processing, the processing unit 160 stays in a standby state until measurement timing comes (NO in step a1). For example, when measurement is performed every 1 minute, the processing unit 160 determines that the measurement timing comes at a point when 1 minute elapses from the last measurement timing.

When the measurement timing comes (YES in step a1), the processing unit 160 acquires meal information (step a3) and acquires insulin administration information (step a5). For example, the processing unit 160 checks, every time the measurement timing comes, whether an operation input concerning whether a meal is started and a selection operation input for a meal menu are performed and acquires meal information including the start of the meal and the meal menu according to the operation inputs. Similarly, the processing unit 160 checks, every time the measurement timing comes, whether an operation input concerning whether insulin is administered and acquires insulin administration information including the administration of insulin according to the operation input. When the operation inputs related to the meal and the insulin administration are not performed, the processing unit 160 determines that both the operation inputs are not performed. The processing unit 160 generates measurement result data concerning the measurement of this time and sets the present time as measurement date and time. If there are the meal information acquired in step a3 and the insulin administration information acquired in step a5, the processing unit 160 sets the meal information and the insulin administration information.

Subsequently, the processing unit 160 determines whether image acquisition time comes. When determining that the image acquisition time comes (YES in step a7), the processing shifts to step a9. When the image acquisition time does not come (NO in step a7), the processing shifts to step a15. For example, the image acquisition timing may be 10 minutes or may be 1 hour. However, if an interval of the image acquisition timing is set short, a biological image is frequently acquired, and a blood vessel position is acquired, measurement accuracy can be maintained. On the other hand, as the interval is set longer, power consumption can be further suppressed. However, for example, when a blood vessel position under the skin does not coincide with the acquired blood vessel position because, for example, the blood vessel moves or when the blood vessel cannot be correctly specified, it could occur that the measurement accuracy until the next acquisition of a blood vessel position is deteriorated. The image acquisition timing is set as appropriate taking into account such a situation.

In step a9, the light-emission control unit 161 causes the light emitting elements 52 of the sensor module 50 to emit lights all at once. The light-reception control unit 162 causes all the light receiving elements 54 to receive (photograph) the lights and acquires a biological image. Subsequently, the blood-vessel-position acquiring unit 163 processes the biological information, acquires a blood vessel position viewed from the skin surface, and selects a blood vessel portion to be set as a measurement target region (step a11). For example, the blood-vessel-position acquiring unit 163 compares each of pixels of the obtained biological image (a luminance image) with reference luminance, performs binarization and filter processing, and acquires a blood vessel position. Pixels having luminance lower than the reference luminance indicate a blood vessel. The blood-vessel-position acquiring unit 163 excludes an accuracy deterioration factor region and selects a blood vessel portion having length equal to or larger than the predetermined minimum region length. The acquired blood vessel position and the position of the selected blood vessel portion are stored in the storing unit 180 as blood vessel position information 200.

Subsequently, the measurement-point-candidate setting unit 164 performs measurement point candidate setting processing, sets a plurality of measurement point candidates in the blood vessel portion selected in step a11, and selects a light emitting position, a light receiving position for measurement, and a light receiving position for reference (step a13). In this case, the measurement-point-candidate setting unit 164 allocates measurement point candidate numbers to the measurement point candidates and associates light emitting element numbers of the light emitting elements for measurement 52-1, light receiving element numbers of the light receiving elements for measurement 54-1, and light receiving element numbers of the light receiving elements for reference 54-2 to generate the measurement point candidate list 210.

In step a15, the exercise-state determining unit 165 calculates exercise intensity of the user 2 on the basis of the detected acceleration input from the acceleration sensor 27. The exercise-state determining unit 165 performs threshold processing of the exercise intensity. When the exercise intensity is equal to or larger than a predetermined threshold set in advance, the exercise-state determining unit 165 determines that the user 2 is "exercising". In this case, the exercise-state determining unit 165 sets the calculated exercise intensity in measurement result data concerning the measurement of this time.

Figure 16:
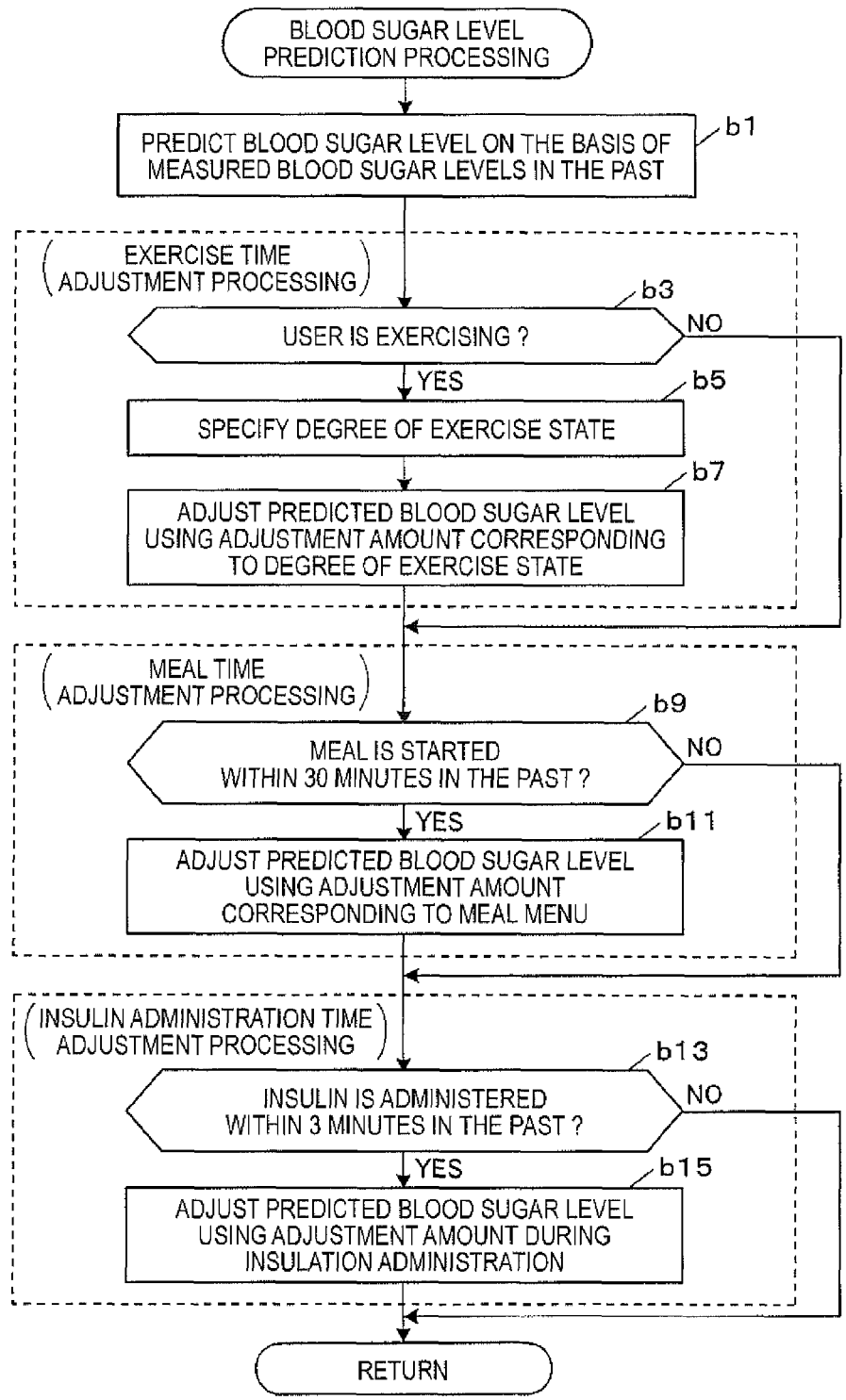
FIG. 16 is a flowchart for explaining a detailed processing procedure of blood sugar level prediction processing.

Thereafter, the blood-sugar-level predicting unit 166 performs blood sugar level prediction processing (step a11). After the blood sugar level prediction processing is performed, the processing shifts to step a19. FIG. 16 is a flowchart for explaining a detailed processing procedure of the blood sugar level prediction processing.

As shown in FIG. 16, in the blood sugar level prediction processing, first, the blood-sugar-level predicting unit 166 predicts the present blood sugar level of the user 2 on the basis of a transition of measured blood sugar levels in the past (step b1). For example, the blood-sugar-level predicting unit 166 refers to the measurement result DB 240 and reads out measured blood sugar levels for a predetermined time in the past. The blood-sugar-level predicting unit 166 calculates, using a publicly-known method such as an extrapolation method, a predicted blood sugar level according to an extrapolation straight line calculated on the basis of the read-out blood sugar levels. The blood-sugar-level predicting unit 166 may calculate an extrapolation curved line to calculate a predicted blood sugar level.

Subsequently, the adjusting unit 167 performs processing in steps b3 to b7 as exercise time adjustment processing. When it is determined in step a15 in FIG. 15 that an exercise state is "exercising" (YES in step b3), the adjusting unit 167 refers to the exercise intensity of the user 2 set in the measurement result DB 240 dating back to values in the past from a value of this time and specifies a degree of the exercise state of the user 2 according to which adjustment condition set in the adjustment table for exercise time 191 is satisfied (step b5). The adjusting unit 167 subtracts an adjustment amount corresponding to the specified degree of the exercise state of the user 2 from the predicted blood sugar level predicted in step b1 and adjusts the predicted blood sugar level (step b7).

Subsequently, the adjusting unit 167 performs processing in steps b9 and b11 as meal time adjustment processing. That is, first, the adjusting unit 167 refers to the meal information of the user set in the measurement result DB 240 dating back to values in the past from a value of this time and determines on the basis of most recent meal information whether a predetermined time (in the first embodiment, 30 minutes in the past) elapses from the start of a meal. When determining that the predetermined time does not elapse and it is the meal time (YES in step b9), the adjusting unit 167 reads out an adjustment value corresponding to a meal menu from the adjustment table for meal time 193 and adds the adjustment value to the predicted blood sugar level predicted in step b1 to adjust the predicted blood sugar level (step b11).

Subsequently, the adjusting unit 167 performs processing in steps b13 and b15 as insulin administration time adjustment processing. That is, first, the adjusting unit 167 refers to the insulin administration information of the user 2 set in the measurement result DB 240 dating back to values in the past from a value of this time and determines on the basis of most recent insulin administration information whether a predetermined time (in the first embodiment, 3 minutes in the past) elapses from the administration of insulin. When determining that the predetermined time does not elapse and it is the insulin administration time (YES in step b13), the adjusting unit 167 reads out an adjustment value from the adjustment table for insulin administration time 195 and subtracts the adjustment value from the predicted blood sugar level predicted in step b1 to adjust the predicted blood sugar level (step b15).

In step a19 in FIG. 15, the light-amount-control-method determining unit 168 applies the first light amount control method or the second light amount control method according to the light amount control method list 186 and determines the number of light emitting elements. Specifically, when the predicted blood sugar level is smaller than a predetermined threshold and is low, the light-amount-control-method determining unit 168 selects the first light amount control method. When the predicted blood sugar level is equal to or larger than the predetermined threshold and is high, light-amount-control-method determining unit 168 selects the second light amount control method. By selecting the first light amount control method or the second light amount control method on the basis of the predicted blood sugar level in this way, the light-amount-control-method determining unit 168 determines the number of light emitting elements in the case of the high predicted blood sugar level as a number smaller than the number of light emitting elements in the case of the low predicted blood sugar level.

Subsequently, the measurement-point selecting unit 169 refers to the measurement point candidate list 210 and selects, as measurement points, measurement point candidates equivalent to the number of light emitting elements determined in step a19 (step a21). In this case, the measurement-point selecting unit 169 allocates measurement point numbers to the selected measurement points and associates the light emitting positions, the light receiving positions for measurement, and the light emitting positions for reference set in the measurement point candidate list 210 with the measurement point numbers to generate the light emitting and light receiving position list 220.

Concerning which of the measurement point candidates are set as the measurement points, a configuration may be adopted in which the measurement point candidates equivalent to the number of light emitting elements may be selected in the order of the measurement point candidate list 210 or the measurement point candidates equivalent to the number of light emitting elements may be selected from the measurement point candidate list 210 at random. Alternatively, a configuration may be adopted in which, when the measurement point candidate list 210 is generated in step a13, processing for rearranging the measurement point candidates in order from the measurement point candidates, the positions of which on the blood vessel portions are closest to the centers, is performed in advance, and the measurement point candidates closer to the centers are more preferentially selected than the measurement point candidates set at the ends of the blood vessel portions.

In the subsequent step a23, the measurement-point selecting unit 169 performs blood sugar level measurement processing using the light emitting and light receiving position list 220. After the blood sugar level measurement processing is performed, the processing shifts to step a25.

Figure 17:
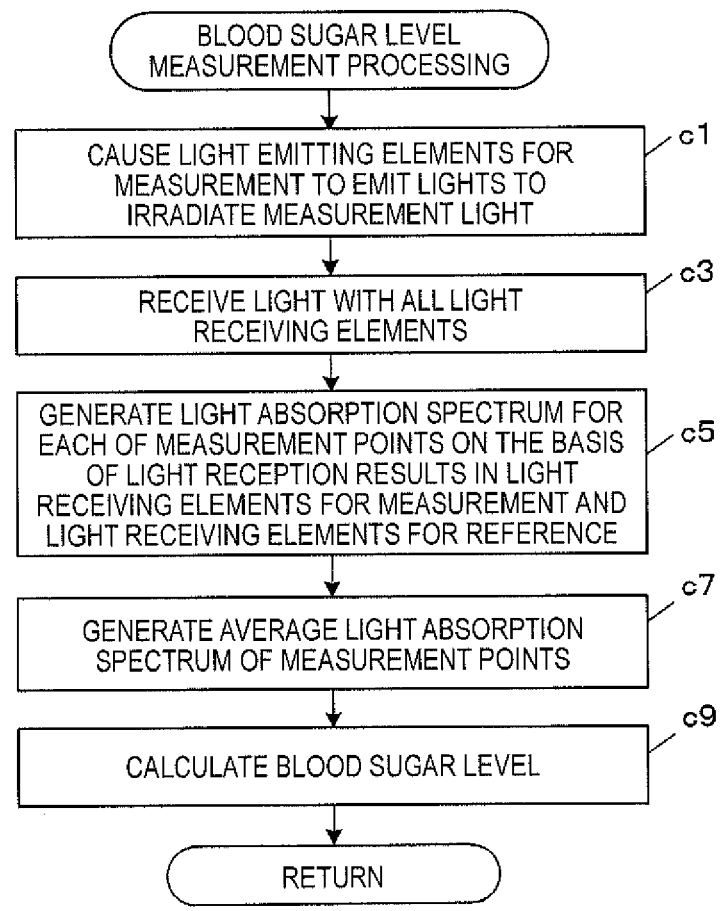
FIG. 17 is a flowchart for explaining a detailed processing procedure of blood sugar level measurement processing.

FIG. 17 is a flowchart for explaining a detailed processing procedure of the blood sugar level measurement processing. As shown in FIG. 17, in the blood sugar level measurement processing, the light-emission control unit 161 causes the light emitting elements 52 for measurement to emit lights all at once to irradiate measurement light according to the light emitting and light receiving position list 220 (step c1). The light-reception control unit 162 causes all the light receiving elements 54 to receive reflected light from the user 2 (step c3). Subsequently, the light-absorption-spectrum generating unit 170 generates a light absorption spectrum for each of the measurement points on the basis of light reception results in the light receiving positions for measurement and the light receiving positions for reference corresponding to the light receiving elements 54 (step c5) and generates an average light absorption spectrum obtained by averaging the generated light absorption spectra at the measurement points (step c7). Spectrum data of the generated average light absorption spectrum is stored in the storing unit 180 as the light absorption spectrum data 230. The blood-sugar-level calculating unit 171 calculates a blood sugar level from the average light absorption spectrum generated in step c7 (step c9). In this case, the blood-sugar-level calculating unit 171 sets the calculated blood sugar level as a measured blood sugar level and sets the measured blood sugar level in measurement result data concerning the measurement of this time.

In step a25 in FIG. 15, the processing unit 160 performs control for reading out, referring to the measurement result DB 240, a measured blood sugar level from the latest measurement result data and displaying the measured blood sugar level of this time on the display unit 140. Thereafter, until the measurement ends (No in step a27), the processing unit 160 returns to step a1 and repeats the processing explained above.

As explained above, according to the first embodiment, it is possible to calculate a predicted blood sugar level from a transition of measured blood sugar levels measured in the past and adjust the predicted blood sugar level taking into account exercise intensity, meal information acquired by receiving an operation input of the user 2, and insulin administration information. Therefore, it is possible to accurately predict the present blood sugar level of the user 2. When the predicted blood sugar level is low, the number of light emitting elements caused to emit light in measurement can be set large. When the predicted blood sugar level is high, the number of light emitting elements caused to emit light in measurement can be set small. Consequently, it is possible to highly accurately perform the measurement when the predicted blood sugar level is low and, on the other hand, reduce a light amount per one measurement and suppress power consumption when the predicted blood sugar level is high. Therefore, it is possible to attain a reduction in power consumption. As a result, even in a form of use of the blood sugar level measuring device 10 mounted on the user 2 to repeatedly measure blood sugar levels for a long period, for example, when a blood sugar level of a diabetic is monitored, it is possible to use the blood sugar level measuring device 10 for a longer period. Labors and time for charging work, battery replacement work, and the like by the user 2 are saved.

Second Embodiment

A second embodiment can be basically realized in the same manner as the first embodiment. However, the second embodiment is different from the first embodiment in that a prediction error of a predicted blood sugar level is calculated on the basis of a measured blood sugar level obtained when the second light amount control method explained in the first embodiment is applied and, when the prediction error is large, the second light amount control method is applied to measure a blood sugar level again.

Functional Configuration

Figure 18:
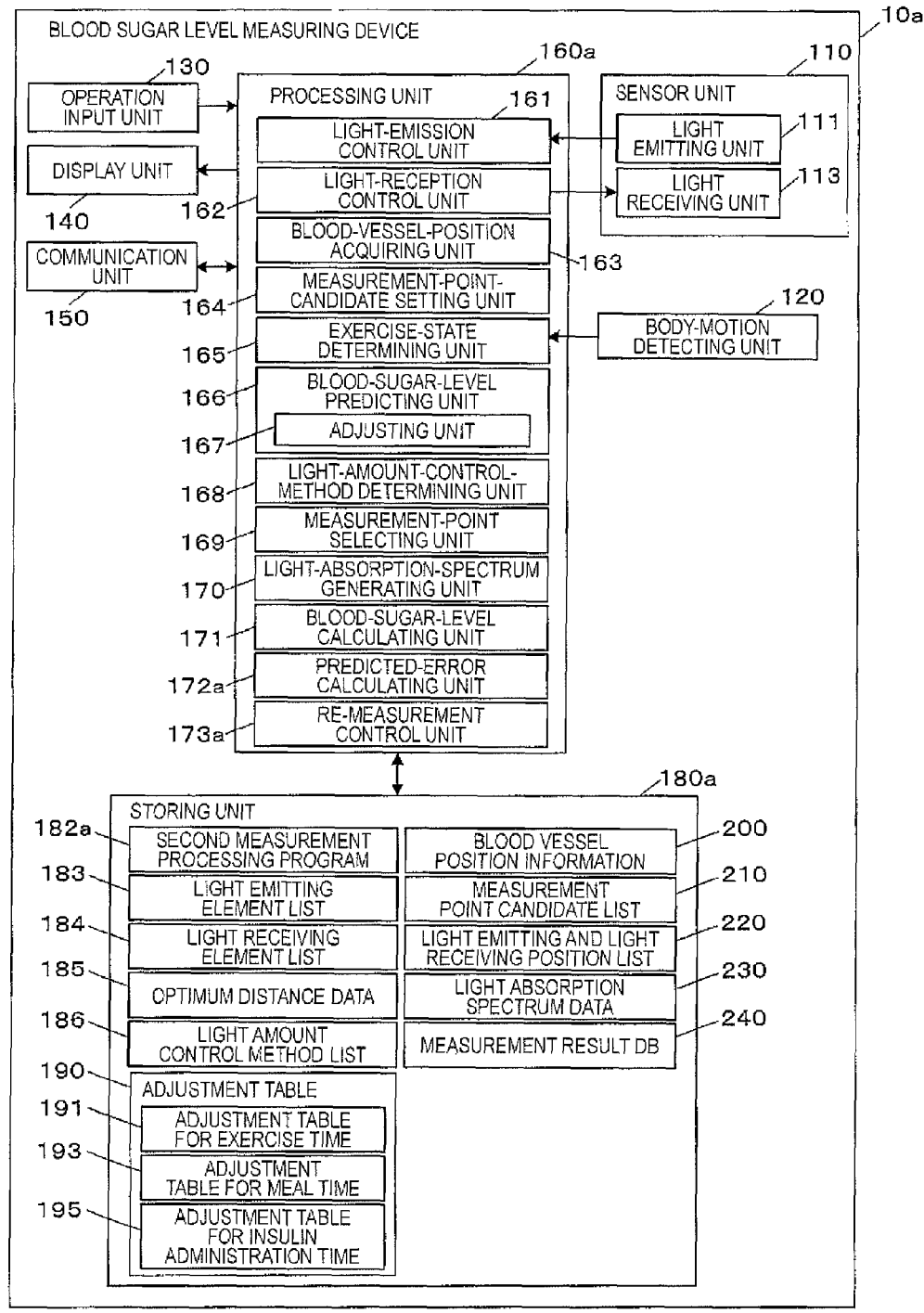
FIG. 18 is a block diagram showing a functional configuration example of a blood sugar level measuring device in a second embodiment.

FIG. 18 is a block diagram showing a main functional configuration example of a blood sugar level measuring device 10a in the second embodiment. As shown in FIG. 18, the blood sugar level measuring device 10a includes the sensor unit 110, the body-motion detecting unit 120, the operation input unit 130, the display unit 140, the communication unit 150, a processing unit 160a, and a storing unit 180a. Note that portions same as those in the first embodiment are denoted by the same reference numerals and signs.

In the second embodiment, the processing unit 160a includes the light-emission control unit 161, the light-reception control unit 162, the blood-vessel-position acquiring unit 163, the measurement-point-candidate setting unit 164, the exercise-state determining unit 165, the blood-sugar-level predicting unit 166 functioning as a predicting unit, the light-amount-control-method determining unit 168, the measurement-point selecting unit 169, the light-absorption-spectrum generating unit 170, the blood-sugar-level calculating unit 171, a prediction-error calculating unit 172a functioning as an error calculating unit, and a re-measurement control unit 173a.

The prediction-error calculating unit 172a calculates a prediction error of a predicted blood sugar level on the basis of a measured blood sugar level obtained when measurement of this time is performed by applying the second light amount control method.

When a re-measurement condition, which is a predetermined condition indicating that the prediction error is relatively large, is satisfied, the re-measurement control unit 173a determines the number of light emitting elements again by applying the first light amount control method.

The storing unit 180a stores in advance a second measurement processing program 182a for causing the processing unit 160a to function as the light-emission control unit 161, the light-reception control unit 162, the blood-vessel-position acquiring unit 163, the measurement-point-candidate setting unit 164, the exercise-state determining unit 165, the blood-sugar-level predicting unit 166, the light-amount-control-method determining unit 168, the measurement-point selecting unit 169, the light-absorption-spectrum generating unit 170, the blood-sugar-level calculating unit 171, the prediction-error calculating unit 172a, and the re-measurement control unit 173a and performing second measurement processing (see FIG. 19), the light emitting element list 183, the light receiving element list 184, the optimum distance data 185, the light amount control method list 186, and the adjustment table 190. Further, the storing unit. 180a stores, according to implementation of measurement, the blood vessel position information 200, the measurement point candidate list 210, the light emitting and light receiving position list 220, the light absorption spectrum data 230, and the measurement result DB 240.

Flow of Processing

Figure 19:
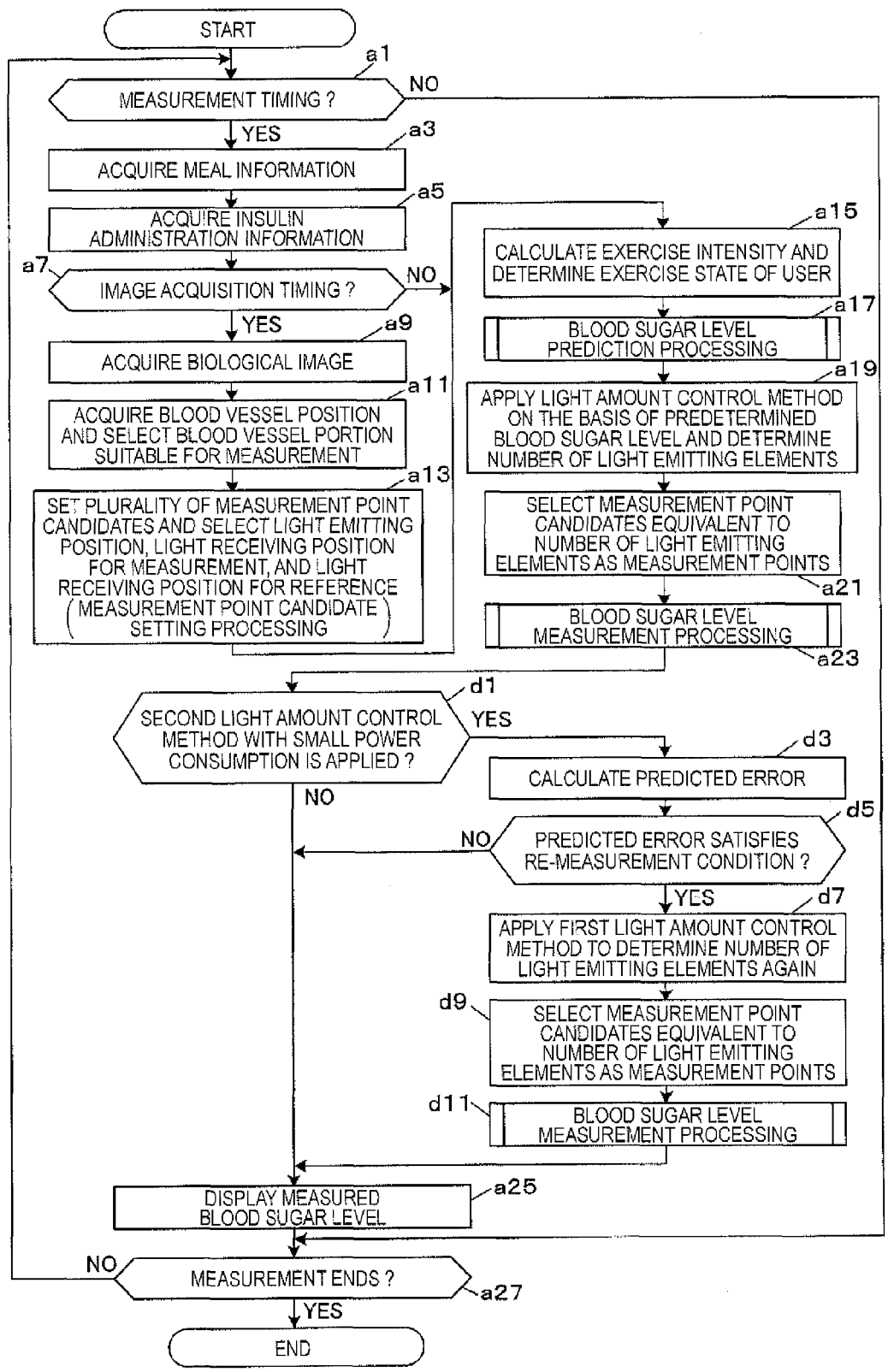
FIG. 19 is a flowchart for explaining a processing procedure of second measurement processing.

FIG. 19 is a flowchart for explaining a processing procedure of the second measurement processing. Note that processing explained below can be realized by the processing unit 160a reading out the second measurement processing program 182a from the storing unit 180a and executing the second measurement processing program 182a.

As shown in FIG. 19, in the second measurement processing, after the blood sugar level measurement processing in step a23, the prediction-error calculating unit 172a determines the light amount control method applied in step a19. When determining that the second light amount control method with small power consumption is applied (YES in step d1), the predicting-error calculating unit 172a calculates an error rate of the predicted blood sugar level as a prediction error on the basis of the measured blood sugar level obtained as a result of step a23 and the predicted blood sugar level obtained as a result of step a11 (step d3). When determining that the first light amount control method is applied (NO in step d1), the processing shifts to step a25.

Subsequently, the re-measurement control unit 173a determines that a re-measurement condition is a condition that the prediction error is not within a predetermined allowable error rate set in advance (e.g., within ±20% considered to belong to the A zone shown in FIG. 3). When the re-measurement condition is satisfied (YES in step d5), the re-measurement control unit 173a determines that the first light amount control method is applied, reads out the number of light emitting elements of the first light amount control method from the light amount control method list 186, and determines the number of light emitting elements again (step d7). When the re-measurement condition is not satisfied (NO in step d5), the processing shifts to step a25.

Thereafter, the measurement-point selecting unit 169 refers to the measurement point candidate list 210 and selects, as measurement points, measurement point candidates equivalent to the number of light emitting elements determined in step d7 again (step d9). The processing is performed in the same procedure as step a21 to generate the light emitting and light receiving position list 220 anew.

In the subsequent step d11, blood sugar level measurement processing is performed using the light emitting and light receiving position list 220 generated anew in step d9. The processing is performed according to the same procedure as step a23 to rewrite the measured blood sugar level of the measurement result data concerning the measurement of this time. Thereafter, the processing shifts to step a25.

As explained above, according to the second embodiment, it is possible to calculate a prediction error of a predicted blood sugar level on the basis of a measured blood sugar level measured by applying the second light amount control method with small power consumption. When the prediction error is relatively large, it is possible to measure a blood sugar level again by applying the first light amount control method in which measurement can be relatively highly accurately performed.

In the embodiments explained above, the light control methods defined by the number of light emitting elements are illustrated. On the other hand, the first light amount control method may be defined as a light amount control method for selecting all measurement point candidates as measurement points rather than defining a specific number as the number of light emitting elements. A light amount control method for selecting a predetermined number of measurement points in order from measurement point candidates, positions of which on the blood vessel portions are closest to the centers from the blood vessel portions (e.g., measurement point candidates closest to the center in the blood vessel longitudinal direction of a certain blood vessel portion 7b in FIG. 9) may be defined as the second light amount control method.

In the embodiments explained above, the two kinds of light amount control methods (the first light amount control method and the second light amount control method) in which the number of light emitting elements is defined in two stages of low or high of the predicted blood sugar level are illustrated. However, the number of light emitting elements may be determined by selectively applying three or more kinds of light amount control methods. In this case, value width of the predicted blood sugar level is finely divided in three or more stages. The three or more kinds of light amount control methods are defined to reduce the number of light emitting elements stepwise as the predicted blood sugar level is higher and are registered in the light amount control method list 186.

In the embodiments explained above, the light amounts control methods are defined by the number of light emitting elements to control a light amount per one measurement. On the other hand, two or more kinds of light amount control methods may be defined by an amount of electric current supplied to the light emitting element for measurement 52-1 to control a light amount per one measurement. For example, an amount of electric current of the second light amount control method applied when a predicted measurement value is high is defined smaller than an amount of electric current of the first light amount control method applied when the predicted measurement value is low. Alternatively, two or more kinds of light amount control methods may be defined by an exposure time to control a light amount per one measurement. For example, an exposure time of the second light amount control method applied when a predicted measurement value is high is defined shorter than an exposure time of the first light amount control method applied when the predicted measurement value is low. If the amount of electric current is reduced, an S/N ratio decreases. Therefore, although measurement accuracy is deteriorated, it is possible to suppress power consumption. The same holds true when the exposure time is reduced.

Alternatively, in the embodiments explained above, in order to generate a light absorption spectrum of blood vessel transmitted light, the light emitting element for measurement 52-1 is caused to emit light while a light emission wavelength is shifted by predetermined wavelength width at a time. However, two or more kinds of light amount control methods may be defined by the predetermined wavelength width (also considered to be a wavelength interval) to control a light amount per one measurement. For example, wavelength width of the second light amount control method applied when a predicted measurement value is high is defined longer than wavelength width of the first light amount control method applied when the predicted measurement value is low. As an example, the wavelength width of the first light amount control method is set to 10 nm and the wavelength width of the second light amount control method is set to 100 nm. When the wavelength width (the wavelength interval) is set long, although it is possible to suppress power consumption, measurement accuracy is deteriorated because data of wavelength at which light is not emitted is interpolated to generate a light absorption spectrum.

Two or more of the number of light emitting elements, the amount of electric current, the exposure time, and the measurement wavelength width (the measurement wavelength interval) may be used to define two or more kinds of light amount control methods according to a combination of the values.

In the embodiments explained above, a predicted blood sugar level is calculated on the basis of a transition of measured blood sugar levels in the past. On the other hand, when a measurement interval is as short as about 1 minute as in the embodiments and blood sugar level fluctuation from the last measurement time is considered to be small, a measured blood sugar level obtained in the last measurement may be predicted as a predicted blood sugar level of this time.

In the embodiments explained above, the body-motion detecting unit 120 is configured by the acceleration sensor 27. Exercise intensity is calculated on the basis of detected acceleration. On the other hand, the body-motion detecting unit 120 may be configured by an angular velocity sensor (a gyro). Exercise intensity may be calculated on the basis of detected angular velocity. Alternatively, the body-motion detecting unit 120 may be configured by a pedometer. Exercise intensity may be calculated on the basis of the number steps (a pitch) per unit time.

What is claimed is:

1. A blood sugar level measuring device comprising:
 a predicting unit configured to predict a blood sugar level of a user;
 a light emitting unit for irradiating measurement light to an inside of a living organism of the user;
 a light-amount control unit configured to control a light amount of the measurement light per one measurement on the basis of the predicted blood sugar level; and
 a measuring unit configured to receive reflected light from the user and measure a blood sugar level.

2. The blood sugar level measuring device according to claim 1, wherein the predicting unit predicts a blood sugar level of the user on the basis of a blood sugar level measured in past by the measuring unit.

3. The blood sugar level measuring device according to claim 2, wherein the predicting unit predicts a blood sugar level of the user on the basis of a transition of the blood sugar level measured in the past.

4. The blood sugar level measuring device according to claim 2, wherein the predicting unit predicts, as a blood sugar level of the user, a blood sugar level measured immediately before the prediction.

5. The blood sugar level measuring device according to claim 1, wherein the predicting unit adjusts the predicted blood sugar level on the basis of at least any one of presence or absence of a meal of the user and presence or absence of insulin administration.

6. The blood sugar level measuring device according to claim 5, wherein the predicting unit adjusts the predicted blood sugar level on the basis of dietary content of the user.

7. The blood sugar level measuring device according to claim 1, further comprising a body-motion detecting unit for detecting a body motion of the user, wherein
 the predicting unit adjusts the predicted blood sugar level on the basis of a detection result of the body-motion detecting unit.

8. The blood sugar level measuring device according to claim 1, wherein the light-amount control unit controls, when the predicted blood sugar level is in a first range, a light amount of the measurement light using a first light amount control method and controls, when the predicted blood sugar level is in a second range higher than the first range, alight amount of the measurement light using a second light amount control method with power consumption smaller than power consumption in the first light amount control method.

9. The blood sugar level measuring device according to claim 8, further comprising an error calculating unit configured to calculate a prediction error of the predicted blood sugar level on the basis of a blood sugar level measured by the measuring unit under the light amount control performed by the light-amount control unit using the second light amount control method, wherein
 when a predetermined condition indicating that the prediction error is relatively large is satisfied, the measuring unit measures a blood sugar level of the user again under the light amount control performed by the light-amount control unit using the first light amount control method.

10. The blood sugar level measuring device according to claim 8, wherein the light amount control methods is defined by at least one of the number of light emitting elements configuring the light emitting unit, an amount of electric current supplied to the light emitting unit, an exposure time of the light emitting unit, and measurement wavelength width of the measurement light.

11. A blood sugar level measuring method comprising:
 predicting a blood sugar level of a user;
 irradiating measurement light to an inside of a living organism of the user;
 controlling a light amount of the measurement light per one measurement on the basis of the predicted blood sugar level; and
 receiving reflected light from the user and measuring a blood sugar level.

* * * * *